United States Patent
Larsson et al.

(10) Patent No.: US 11,896,589 B2
(45) Date of Patent: Feb. 13, 2024

(54) DIAZINYL AMINO ACRIDINES AND MEDICAL USES THEREOF

(71) Applicants: Lars-Gunnar Olof Larsson, Stockholm (SE); Alina Andrea Viktoria Castell, Stockholm (SE)

(72) Inventors: Lars-Gunnar Olof Larsson, Stockholm (SE); Alina Andrea Viktoria Castell, Stockholm (SE)

(73) Assignee: MyCural Therapeutics AB, Uppsala (SE)

(*) Notice: Subject to any disclaimer, the term of this patent is extended or adjusted under 35 U.S.C. 154(b) by 0 days.

(21) Appl. No.: 16/962,620

(22) PCT Filed: Jan. 23, 2019

(86) PCT No.: PCT/EP2019/051664
§ 371 (c)(1),
(2) Date: Jul. 16, 2020

(87) PCT Pub. No.: WO2019/145375
PCT Pub. Date: Aug. 1, 2019

(65) Prior Publication Data
US 2020/0405707 A1    Dec. 31, 2020

(30) Foreign Application Priority Data

Jan. 23, 2018    (GB) ..................................... 1801102

(51) Int. Cl.
| A61K 31/473 | (2006.01) |
| A61P 35/00 | (2006.01) |
| C07D 215/42 | (2006.01) |
| C07D 401/12 | (2006.01) |
| C07D 495/04 | (2006.01) |

(52) U.S. Cl.
CPC ............ *A61K 31/473* (2013.01); *A61P 35/00* (2018.01); *C07D 215/42* (2013.01); *C07D 401/12* (2013.01); *C07D 495/04* (2013.01)

(58) Field of Classification Search
CPC .................................................. A61K 31/473
See application file for complete search history.

(56) References Cited

U.S. PATENT DOCUMENTS 2,318,968 A    5/1943    Proescher et al.

FOREIGN PATENT DOCUMENTS

WO    2012/093741 A1    7/2012

OTHER PUBLICATIONS

Bahram et al., Interferon-γ-induced p27KIP1 binds to and targets MYC for proteasome-mediated degradation. Oncotarget. Jan. 19, 2016;7(3):2837-54.
Ismayilov, Associates of the Bromide of Mercury (II) of Etoxyakridines Azoderivatives and Their Use in Photometric Analysis. Kimya Problemlari Jurnali. 2006;1:153-156.
Mateyak et al., Phenotypes of c-Myc-deficient rat fibroblasts isolated by targeted homologous recombination. Cell Growth Differ. Oct. 1997;8(10):1039-48.
Remy et al., A highly sensitive protein-protein interaction assay based on Gaussia luciferase. Nat Methods. Dec. 2006;3(12):977-9.
Seidel et al., Microscale thermophoresis quantifies biomolecular interactions under previously challenging conditions. Methods. Mar. 2013;59(3):301-15.
Soderberg et al., Direct observation of individual endogenous protein complexes in situ by proximity ligation. Nat Methods. Dec. 2006;3(12):995-1000.
Arkin et al., Small-molecule inhibitors of protein-protein interactions: progressing toward the reality. Chem Biol. Sep. 18, 2014;21(9):1102-14.
Blackwood et al., Max: a helix-loop-helix zipper protein that forms a sequence-specific DNA-binding complex with Myc. Science. Mar. 8, 1991;251(4998):1211-7.
Fillippakopoulos et al., Selective inhibition of BET bromodomains. Nature. Dec. 23, 2010;468(7327):1067-73.
Giorello et al., Inhibition of cancer cell growth and c-Myc transcriptional activity by a c-Myc helix 1-type peptide fused to an internalization sequence. Cancer Res. Aug. 15, 1998;58(16):3654-9.
Mckeown et al., Therapeutic Strategies to Inhibit MYC. Cold Spring Harbor Perspectives in Medicine. doi: 10.1101/cshperspect. a014266. 17 pages, (2014).
Metallo, Intrinsically disordered proteins are potential drug targets. Curr Opin Chem Biol. Aug. 2010;14(4):481-8.
Meyer et al., Reflecting on 25 years with MYC. Nat Rev Cancer. Dec. 2008;8(12):976-90.
Nair et al., X-ray structures of Myc-Max and Mad-Max recognizing DNA. Molecular bases of regulation by proto-oncogenic transcription factors. Cell. Jan. 24, 2003;112(2):193-205.
Nero et al., Oncogenic protein interfaces: small molecules, big challenges. Nat Rev Cancer. Apr. 2014;14(4):248-62.
Soucek et al., Modelling Myc inhibition as a cancer therapy. Nature. Oct. 2, 2008;455(7213):679-83.

(Continued)

*Primary Examiner* — Brian E Mcdowell
(74) *Attorney, Agent, or Firm* — McCarter & English, LLP; Steven G. Davis; Michael J. DeGrazia

(57) ABSTRACT

There is provided herein compounds of formula (I) and pharmaceutically-acceptable salts and/or detectably-labelled derivatives thereof, wherein $R^1$ to $R^3$, X, Y, n and m have meanings as provided in the description, together with formulations and products comprising the same. There is also provided the use of such compounds, formulations and products in the treatment of cancers characterised by increased MYC activity.

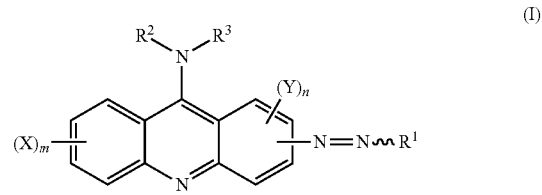

(I)

12 Claims, 7 Drawing Sheets

(56) References Cited

OTHER PUBLICATIONS

Tse et al., ABT-263: a potent and orally bioavailable Bcl-2 family inhibitor. Cancer Res. May 1, 2008;68(9):3421-8.

Vassilev et al., In vivo activation of the p53 pathway by small-molecule antagonists of MDM2. Science. Feb. 6, 2004;303(5659):844-8.

Zinzalla et al., Targeting protein-protein interactions for therapeutic intervention: a challenge for the future. Future Med Chem. Apr. 2009;1(1):65-93.

Bouffier et al., Functionalization of the A ring of pyridoacridine as a route toward greater structural diversity. Synthesis of an octacyclic analogue of eilatin. Bioorg Med Chem Lett. Aug. 15, 2009;19(16):4836-8.

Dinica et al., Regioselective synthesis of angular nitrogen polyheterocycles: dipyrido[3,2-a:2',3'-c]quinolino[2,3-h] phenazines. Tetrahedron Letters. Oct. 28, 2002;43(44):7883-7885.

Fletcher et al., Small-molecule inhibitors of the Myc oncoprotein. Biochim Biophys Acta. May 2015;1849(5):525-43.

Jeney et al., Chemotherapeutische Studien in der Reihe der heterozyklischen azo-verbindungen. II. Aryl-azo-Derivative der N1-Heterozyklyl-sulphonamide. Zentralblatt fuer bakteriologie, Parasitenkunde, Infektionskranskeiten und hygiene. 1960;180:96-112.

Mohrle et al., Reaction of ethacridine lactate with nitrous acid and the colour-structure relationships with acridine derivatives Part 3: Analytics of ethacridine lactate. Pharmazie. 1997;52(8):603-611.

Park et al., Novel small-molecule inhibitors of Bcl-XL to treat lung cancer. Cancer Res. Sep. 1, 2013;73(17):5485-96.

Sassano et al., Identification of G-Quadruplex Inducers Usinga Simple, Inexpensiveand Rapid High Throughput Assay, and TheirInhibition of Human Telomerase. Open Med Chem J. 2012;6:20-8.

Tatsuoka et al., Studies on Antimalarials. VIII. Syntheses of Antimalarials with Azo-groups. Ann Rept Takeda Research Lab. 1951;10:16-32.

Wisniewska et al., Diminished toxicity of C-1748, 4-methyl-9-hydroxyethylamino-1-nitroacridine, compared with its demethyl analog, C-857, corresponds to its resistance to metabolism in HepG2 cells. Biochem Pharmacol. Jul. 1, 2012;84(1):30-42.

International Search Report and Written Opinion for Application No. PCT/EP2019/051664, dated Jun. 4, 2019, 17 pages.

Kim et al., Anti-tumor effects by a synthetic chalcone compound is mediated by c-Myc-mediated reactive oxygen species production. Chem Biol Interact. Oct. 6, 2010;188(1):111-8.

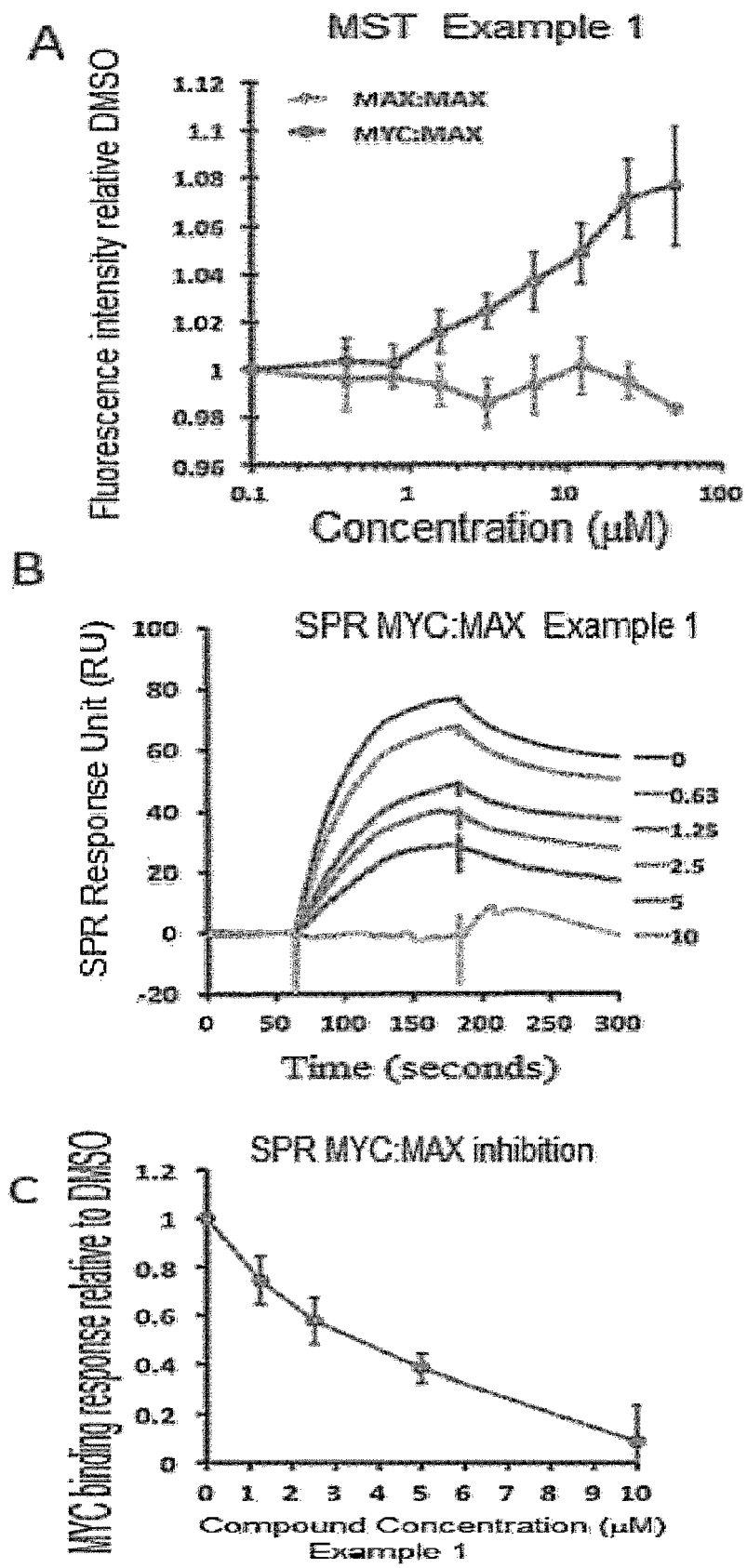
Figure 1 A-C

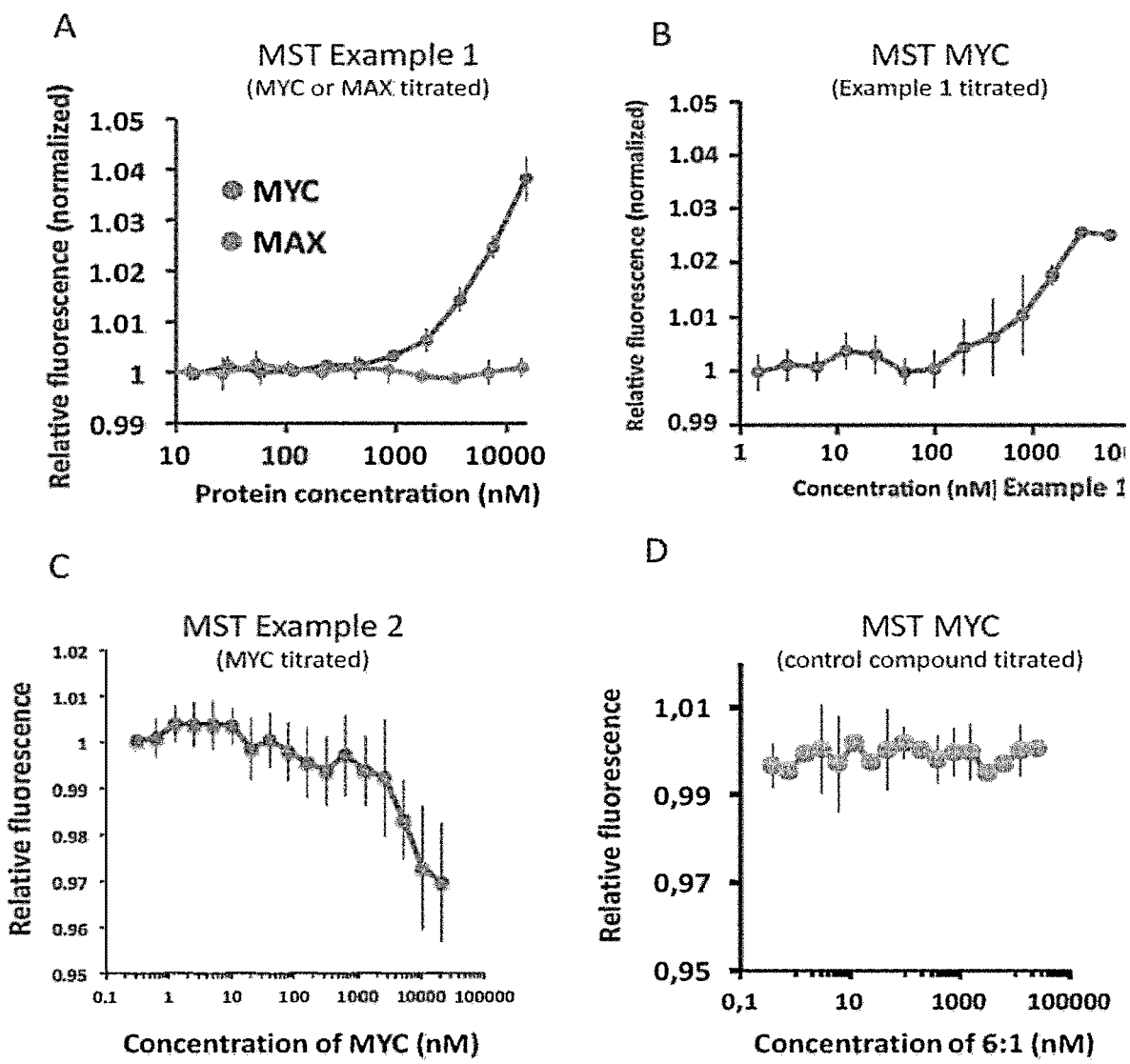
Figure 2 A-D

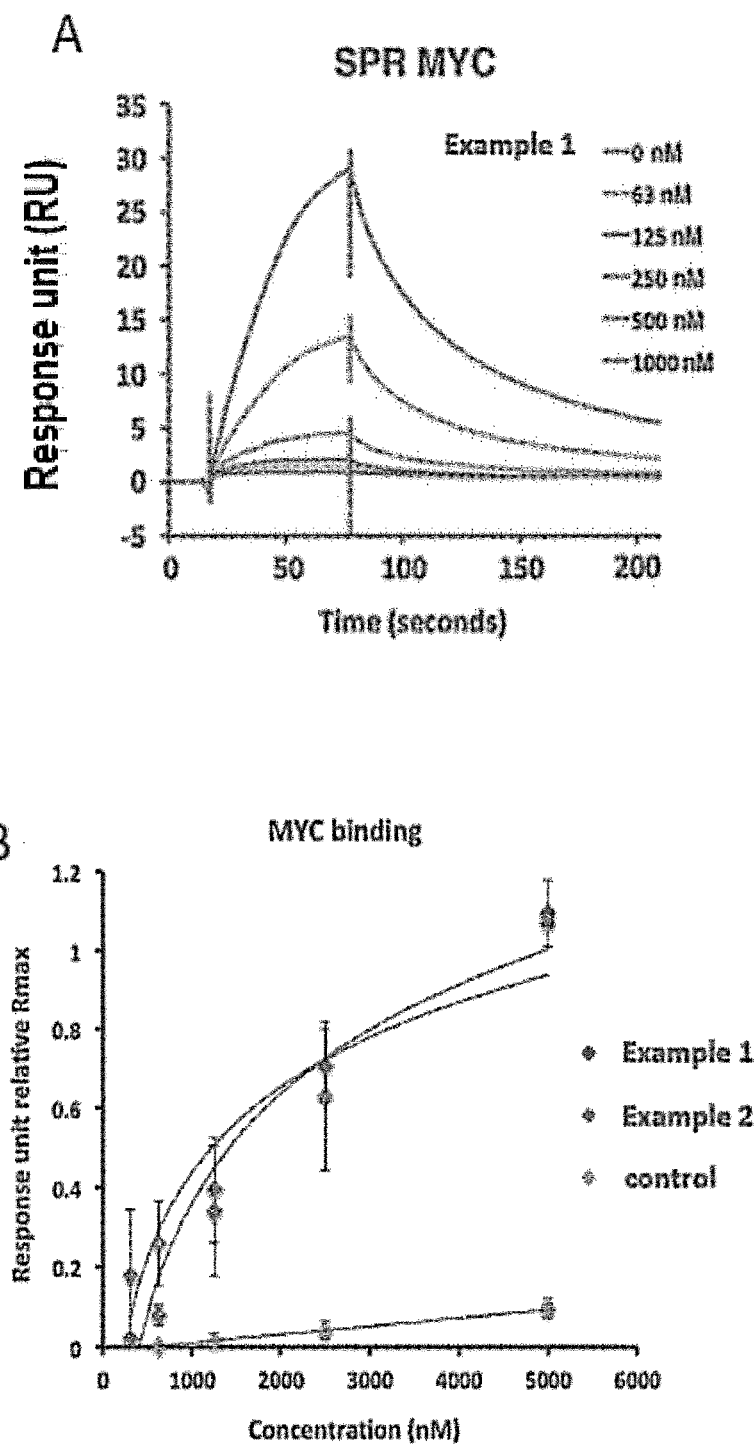
Figure 3 A-B

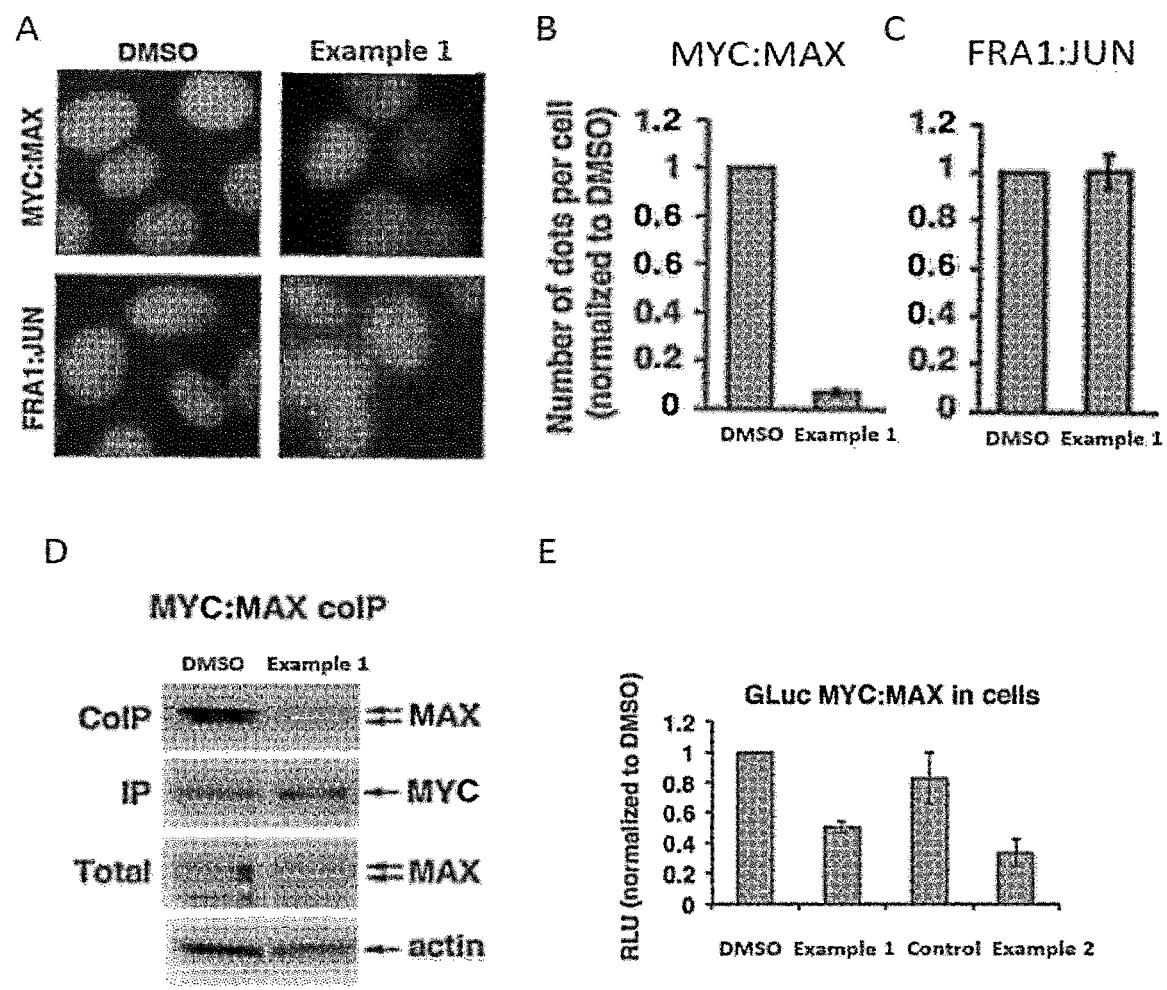
Figure 4 A-E

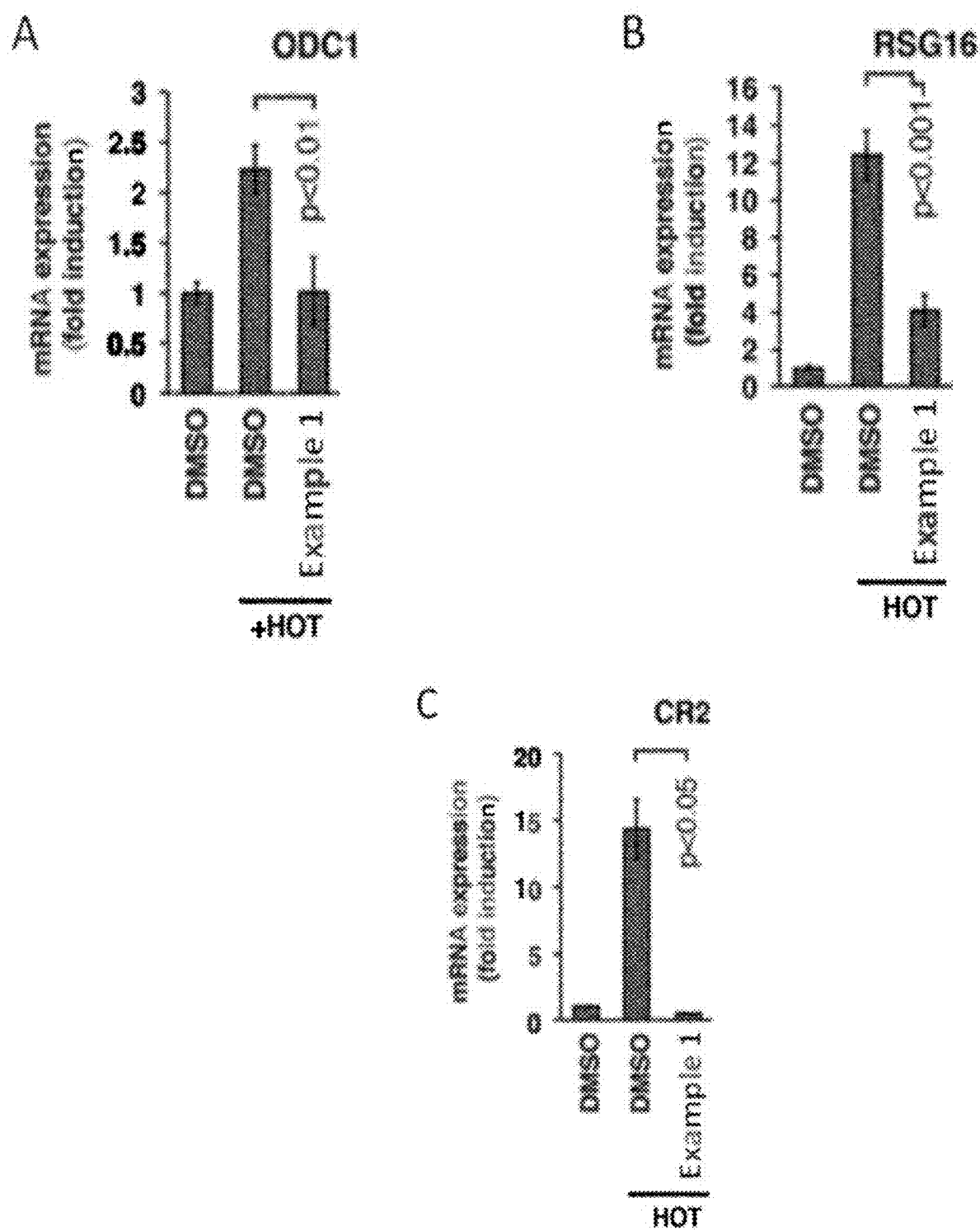
Figure 5 A-C

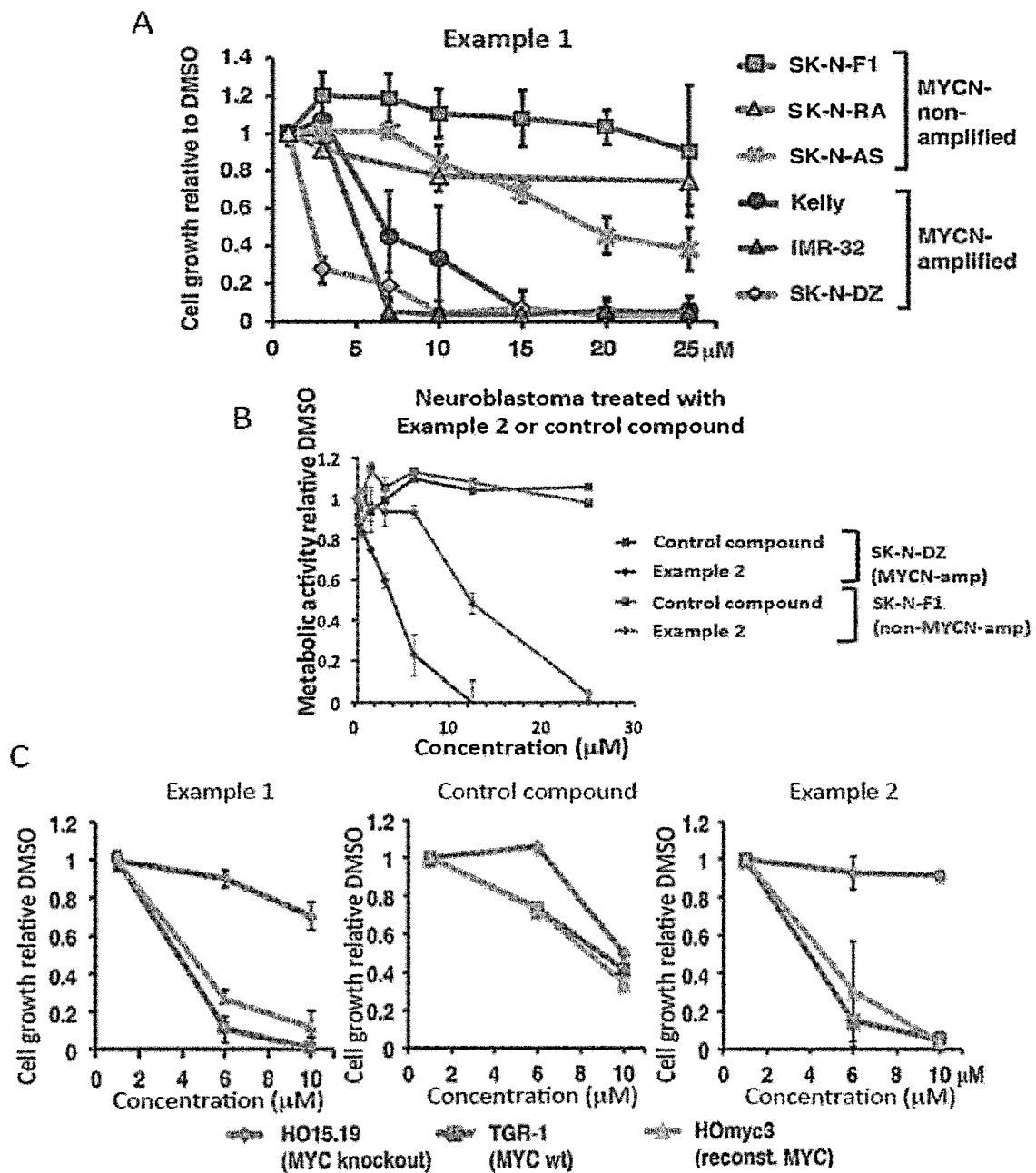
Figure 6 A-C

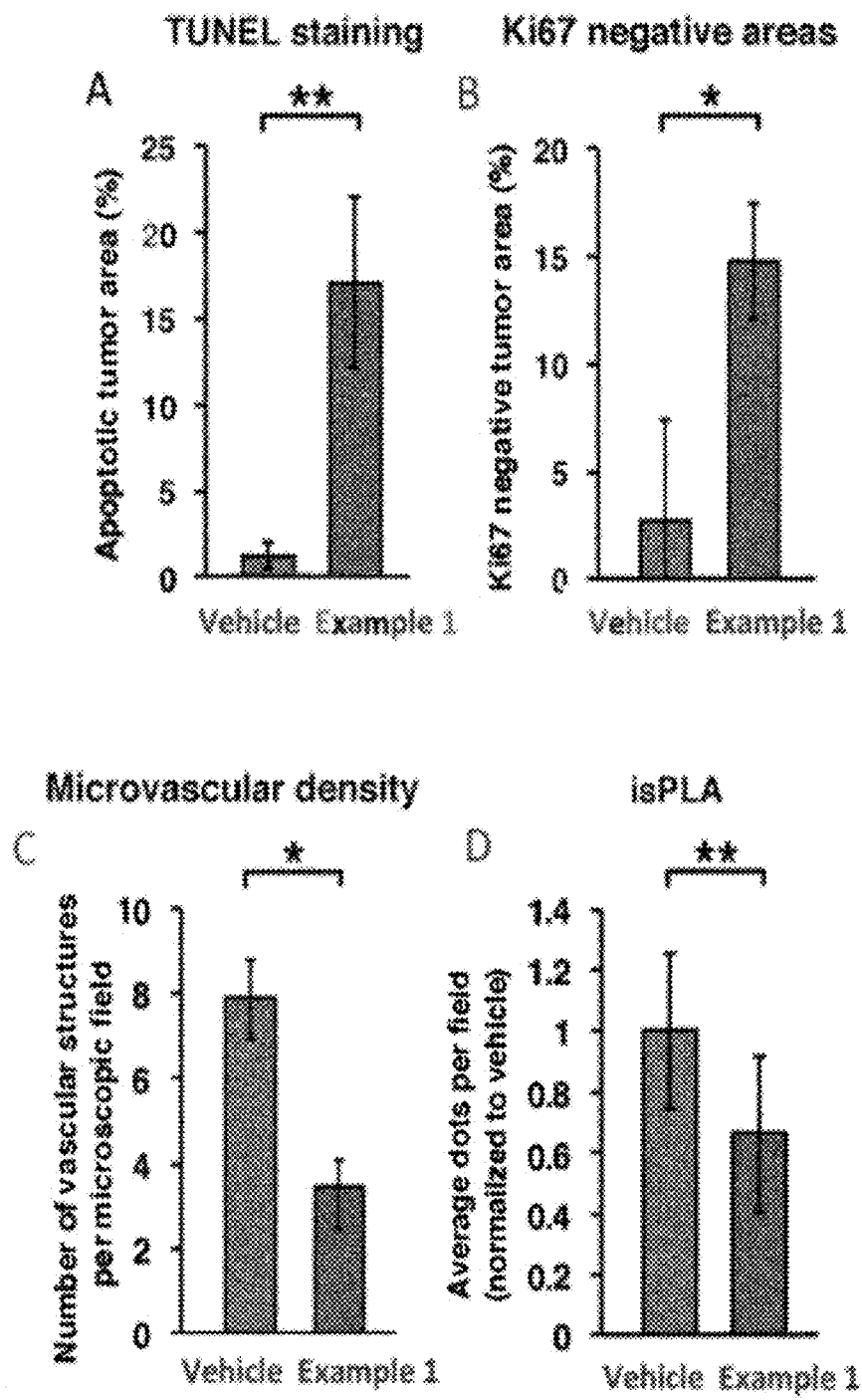
Figure 7 A-D

DIAZINYL AMINO ACRIDINES AND MEDICAL USES THEREOF

CROSS-REFERENCE TO RELATED APPLICATIONS

This application is a U.S. national stage filing, under 35 U.S.C. § 371(c), of International Application No. PCT/EP2019/051664, filed on Jan. 23, 2019, which claims priority to United Kingdom Patent Application No. 1801102.3, filed on Jan. 23, 2018.

FIELD OF THE INVENTION

The present invention relates to novel compounds, compositions comprising such compounds, and the use of such compounds and compositions in medicine. In particular, the present invention relates to the use of such compounds and compositions in methods for the treatment of cancers, particularly cancers characterised by increased activity of the MYC pathway, which treatment is thought to occur through specific and potent inhibition of MYC:MAX interaction.

BACKGROUND OF THE INVENTION

The listing or discussion of an apparently prior-published document in this specification should not necessarily be taken as an acknowledgement that the document is part of the state of the art or is common general knowledge.

The MYC family of oncogenes, consisting of MYC, MYCN and MYCL (here collectively referred to as "MYC"), encodes basic helix-loop-helix leucine zipper (bHLHZip) transcription factors (Meyer, N. & Penn, L. Z., *Nat Rev Cancer*, 8, 976-990 (2008)).

Through the HLHZip domain, MYC heterodimerizes with the bHLHZip protein MAX, which enables the MYC:MAX complex to bind E-box regulatory DNA elements throughout the genome, thereby controlling transcription of a large group of specific genes. The direct target gene products in turn influences global RNA and protein synthesis, thereby coordinating multiple fundamental cellular processes, including cell cycle progression, cell growth, apoptosis, senescence, metabolism and stem cell functions. In addition to MAX, MYC interacts with a plethora of other proteins carrying out different functions in gene regulation. Deregulation of expression of MYC family genes/proteins occurs in over half of all human tumors, and can be caused by chromosomal aberrations affecting the MYC loci, such as translocation and gene amplification, or can be due to oncogenic aberrations affecting upstream regulators of MYC. Abnormal MYC expression is often correlated with aggressive disease, resistance to therapy and poor prognosis, and MYC is therefore considered as one of the most important drivers of tumor development. Evidence from mouse models has shown that elimination of MYC using genetic tools often causes complete and irreversible tumor regression with well-tolerated and reversible side effects, suggesting that MYC would be a suitable target for cancer therapy (Soucek, L. et al., *Nature*, 455, 679-683 (2008)). However, so far there are no specific anti-MYC drugs available in the clinic.

Although MYC has previously been considered "undruggable", a number of efforts have been made during recent years to target MYC. MYC expression is sensitive to BET bromodomain inhibitors and to protein translation inhibitors in certain cells. Alternatively, kinases regulating MYC activity and turnover, druggable key downstream MYC target gene products or synthetic lethal interactions involving MYC can be targeted (McKeown, M. R. & Bradner, J. E., *Cold Spring Harb Perspect Med*, 4, (2014)). However, these approaches are not specific for MYC, are context-dependent, and are presumably bound to fail eventually due to selection of alternative pathways regulating MYC expression and activity in tumor cells.

While these strategies all target MYC indirectly, several efforts to target the MYC protein directly have also been reported (Fletcher, S. & Prochownik, E. V., *Biochim Biophys Acta* 1849, 525-543 (2015)). Since MYC is strictly dependent on MAX for binding E-boxes, targeting MYC:MAX or MYC:MAX:DNA interactions are therefore a conceivable approach to target MYC activity (Blackwood, E. M. & Eisenman, R. N., *Science* 251, 1211-1217 (1991)). This suggests that the MYC:MAX heterodimer could be a potential drug target in vivo. However, targeting protein-protein interactions (PPI) is challenging due to presumed large, flat interactions surfaces lacking pockets amenable for small-molecule binding (Nero et al., 2014). In addition, the monomeric MYC bHLHZip domain is intrinsically disordered, and adopts an α-helical HLHZip fold upon dimerization with MAX (Metallo, 2010; Nair and Burley, 2003). Nevertheless, it has become clear that PPIs often involve "hot spots" engaging a small number, or cluster, of residues where most of the binding energy is localized, and therefore potentially druggable with small molecules (Nero, T. L., Morton, C. J., Holien, J. K., Wielens, J. & Parker, M. W., *Nature reviews. Cancer*, 14, 248-262 (2014); Zinzalla, G., and Thurston, D. E., *Future Med Chem*, 1, 65-93 (2009)).

During recent years there have been several reports of successful targeting of protein-protein interactions with small molecules, including Nutlin-3a (targeting p53: MDM2) (Vassilev, L. T. et al., *Science*, 303, 844-848 (2004)), BET inhibitors such as JQ1 (bromodomains:histones) (Filippakopoulos, P. et al., *Nature*, 468, 1067-1073 (2010)) and the BH3 mimetic compound Navitoclax/ABT-263 (BCL-2 family protein interactions) (Tse, C. et al., *Cancer Res*, 68, 3421-3428 (2008)). These compounds, or improved versions, are now in clinical trials, which have encouraged further research on PPIs as drug targets (Arkin, M. R., Tang, Y., and Wells, J. A., *Chemistry & biology*, 21, 1102-1114 (2014); Nero, T. L., Morton, C. J., Holien, J. K., Wielens, J. & Parker, M. W., *Nature reviews. Cancer*, 14, 248-262 (2014)).

Several research groups have attempted to find compounds targeting the MYC:MAX interaction by screening small-molecule libraries using either FRET, or fluorescence polarization in vitro, or by applying yeast-two-hybrid (Y2H) assays (Fletcher, S. & Prochownik, E. V., *Biochim Biophys Acta* 1849, 525-543 (2015)). Another approach has been the design of peptidomimetic molecules targeting MYC:MAX PPIs based on the structures of the HLHZip region of MYC or MAX (Giorello, L. et al., *Cancer Res*, 58, 3654-3659 (1998)). As a result, a number of small molecules have been identified that target the MYC:MAX or MYC:MAX:DNA interaction in vitro and in mammalian cells, and that inhibit MYC-driven tumor cell growth in cell cultures and to some extent in vivo (Fletcher, S. & Prochownik, E. V., *Biochim Biophys Acta* 1849, 525-543 (2015); McKeown, M. R. & Bradner, J. E., *Cold Spring Harb Perspect Med*, 4, (2014)). However, none of these compounds have made their way for clinical studies.

Given this, there exists an urgent need to identify and develop new potent and selective direct MYC inhibitors suitable for in vivo applications, such as for the treatment of cancers.

DETAILED DESCRIPTION OF THE INVENTION

It has now been found that certain diazenyl substituted 9-aminoacridines have surprising properties which render such compounds useful in the treatment of cancers, particularly those cancers characterised by increased activity of the MYC pathway (i.e. increased MYC activity).

In particular, by using a mammalian cell-based MYC: MAX protein interaction screen, it has now surprisingly been found that these 9-aminoacridines strongly interfere with MYC:MAX interaction in cells and in vitro. It has been found that these compounds are unexpectedly able to inhibit MYC-driven transcription by binding MYC directly in vitro, in turn inhibiting MYC-dependent tumor cell growth both in cell cultures and in a MYC-driven mouse xenograft tumor model, while sparing normal cells.

Compounds of the Invention

In a first aspect of the invention, there is provided a compound of formula I

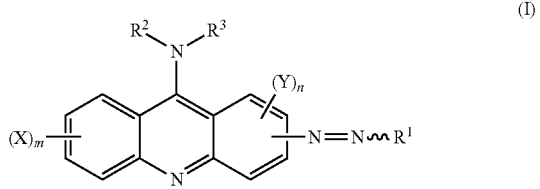

(I)

or a pharmaceutically-acceptable salt and/or detectably-labelled derivative thereof, wherein:

$R^1$ represents $C_{1-12}$ alkyl, $C_{2-12}$ alkenyl or $C_{2-12}$ alkynyl, each optionally substituted by one or more groups independently selected from $G^{1a}$, heterocyclyl optionally substituted by one or more groups independently selected from $G^{1b}$, aryl optionally substituted by one or more groups independently selected from $G^{1c}$, or heteroaryl optionally substituted by one or more groups independently selected from $G^{1d}$;

$R^2$ and $R^3$ each independently represent H, $R^{a1}$, —CN, —S(O)$_p R^{b1}$, —S(O)$_p$N(R$^{c1}$)R$^{d1}$ or —S(O)$_p$OR$^{e1}$;

m represents 1, 2, 3 or 4;

n represents 0, 1, 2 or 3;

each X independently represents independently represents halo, $R^{a2}$, —CN, -A$^{a1}$-C(Q$^{a1}$)R$^{b2}$, -A$^{b1}$-C(Q$^{b1}$)N(R$^{c2}$)R$^{d2}$, -A$^{c1}$-C(Q$^{c1}$)OR$^{e2}$, -A$^{d1}$-S(O)$_p R^{f2}$, -A$^{e1}$-S(O)$_p$N(R$^{g2}$)R$^{h2}$, -A$^{f1}$-S(O)$_p$OR$^{i2}$, —N$_3$, —N(R$^{j2}$)R$^{k2}$, —N(H)CN, —NO$_2$, —ONO$_2$, —OR$^{l2}$, —SR$^{m2}$, —B(OR$^{n2}$)$_2$, —P(O)(N(R$^{o2}$)R$^{p2}$)$_2$, —P(O)(N(R$^{o2}$)R$^{p2}$)(OR$^{q2}$) or —P(O)(OR$^{r2}$)$_2$;

each A$^{a1}$ to A$^{f1}$ independently represents a single bond, —C(O)N(R$^{s2}$)—, —N(R$^{t1}$)— or —O—;

each Q$^{a1}$ to Q$^{c1}$ independently represents =O, =S, =C(H)NO$_2$, =N(CN), =NR$^{u2}$, =NN(R$^{v2}$)R$^{w2}$ or =N(OR$^{x2}$)—; =NS(O)$_p$N(R$^{v1}$)R$^{w2}$;

each Y independently represents halo, $R^{a3}$, —CN, -A$^{a2}$-C(O)R$^{b3}$, -A$^{b2}$-C(O)N(R$^{c3}$)R$^{d3}$, -A$^{c2}$-C(O)OR$^{e3}$, -A$^{d2}$-S(O)R$^{f3}$, -A$^{e2}$-S(O)$_p$N(R$^{g3}$)R$^{h3}$, -A$^{f2}$-S(O)$_p$OR$^{i3}$, —N(R$^3$)R$^{k3}$, —OR$^{l3}$ or —SR$^{m3}$;

each A$^{a2}$ to A$^{f2}$ independently represents a single bond, —N(R$^{n3}$)— or —O—;

each G$^{1a}$ independently represents halo, —CN, -A$^{a3}$-C(Q$^{a2}$)R$^{b4}$, -A$^{b3}$-C(Q$^{b2}$)N(R$^{c4}$)R$^{d4}$, -A$^{c3}$-C(Q$^{c2}$)OR$^{e4}$, -A$^{d3}$-S(O)$_p R^{f4}$, -A$^{e3}$-S(O)$_p$N(R$^{g4}$)R$^{h4}$, -A$^{f3}$-S(O)$_p$OR$^{i4}$, —N$_3$, —N(R$^{j4}$)R$^{k4}$, —N(H)CN, —NO$_2$, —ONO$_2$, —OR$^{l4}$, —SR$^{m4}$—B(OR$^{n4}$)$_2$, —P(O)(N(R$^{o4}$)R$^{p4}$)$_2$, —P(O)(N(R$^{o4}$)R$^{p4}$)(OR$^{q4}$) or —P(O)(OR$^{r4}$)$_2$ or =Q$^{d2}$;

each G$^{1b}$, G$^{1c}$ and G$^{1d}$ independently represents halo, R$^{a4}$, —CN, -A$^{a3}$-C(Q$^{a2}$)R$^{b4}$, -A$^{b3}$-C(Q$^{b2}$)N(R$^{c4}$)R$^{d4}$, -A$^{c3}$-C(Q$^{c2}$)OR$^{e4}$, -A$^{d3}$-S(O)$_p R^{f4}$, -A$^{e3}$-S(O)$_p$N(R$^{g4}$)R$^{h4}$, -A$^{f3}$-S(O)$_p$OR$^{i4}$, —N$_3$, —N(R$^{j4}$)R$^{k4}$, —N(H)CN, —NO$_2$, —ONO$_2$, —OR$^{l4}$, —SR$^{m4}$—B(OR$^{n4}$)$_2$, —P(O)(N(R$^{o4}$)R$^{p4}$)$_2$, —P(O)(N(R$^{o4}$)R$^{p4}$)(OR$^{q4}$) or —P(O)(OR$^{r4}$)$_2$ or =Q$^{d2}$;

each A$^{a3}$ to A$^{f3}$ independently represents a single bond, —C(O)N(R$^{s4}$)—, —N(R$^{t4}$)— or —O—;

each Q$^{a2}$ to Q$^{d2}$ independently represents =O, =S, =C(H)NO$_2$, =N(CN), =NR$^{u4}$, =NN(R$^{v4}$)R$^{w4}$ or =N(OR$^{x4}$), =NS(O)$_p$N(R$^{v4}$)R$^{w4}$;

$R^{a1}$, $R^{b1}$ and $R^{e1}$ represent $C_{1-12}$ alkyl, $C_{2-12}$ alkenyl or $C_{2-12}$ alkynyl, each optionally substituted by one or more groups independently selected from $G^{2a}$, or heterocyclyl optionally substituted by one or more groups independently selected from $G^{2b}$;

$R^{c1}$ and $R^{d1}$ independently represent H, $C_{1-12}$ alkyl, $C_{2-12}$ alkenyl or $C_{2-12}$ alkynyl, each optionally substituted by one or more groups independently selected from $G^{2a}$, or heterocyclyl optionally substituted by one or more groups independently selected from $G^{2b}$, or alternatively $R^{c1}$ and $R^{d1}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl, $C_{2-3}$ alkenyl or $C_{2-3}$ alkynyl each optionally substituted by one or more halo, and =O;

each $R^{a2}$ and $R^{f2}$ independently represents $C_{1-12}$ alkyl, $C_{2-12}$ alkenyl or $C_{2-12}$ alkynyl each optionally substituted by one or more groups independently selected from $G^{3a}$, or heterocyclyl optionally substituted by one or more groups independently selected from $G^{3b}$;

each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$, $R^{o2}$, $R^{p2}$, $R^{q2}$, $R^{r2}$, $R^{s2}$, $R^{t2}$, $R^{u2}$, $R^{v2}$, $R^{w2}$ and $R^{x2}$ independently represents H, $C_{1-12}$ alkyl, $C_{2-12}$ alkenyl or $C_{2-12}$ alkynyl each optionally substituted by one or more groups independently selected from $G^{3a}$, or heterocyclyl optionally substituted by one or more groups independently selected from $G^{3b}$, or alternatively any of $R^{c2}$ and $R^{d2}$, $R^{g2}$ and $R^{h2}$, $R^{j2}$ and $R^{k2}$, $R^{o2}$ and $R^{p2}$ and/or $R^{v2}$ and $R^{w2}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl, $C_{2-3}$ alkenyl or $C_{2-3}$ alkynyl each optionally substituted by one or more halo, and =O, or alternatively any two R$^{n2}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halo, $C_{1-3}$ alkyl optionally substituted by one or more halo, and =O, or alternatively two R$^{r2}$ are linked together to form, along with the phosphorus, and the oxygen atoms to which they are attached, a 5- to 8-membered heterocyclic ring, which ring optionally contains one or more further heteroatoms and which ring optionally is substituted by one or more groups independently selected from halo, $C_{1-3}$ alkyl optionally substituted by one or more halo, and =O;

each R$^{a3}$ and R$^{f3}$ independently represents $C_{1-6}$ alkyl optionally substituted by one or more F;

each R$^{b3}$, R$^{c3}$, R$^{d3}$, R$^{e3}$, R$^{g3}$, R$^{h3}$, R$^{i3}$, R$^{j3}$, R$^{k3}$, R$^{l3}$, R$^{m3}$ and R$^{n3}$ independently represents H or $C_{1-6}$ alkyl optionally substituted by one or more F, or alternatively any of $R^{c3}$ and $R^{cd}$, $R^{fg}$ and $R^{h3}$ and/or $R^{j3}$ and $R^{k3}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $R^{a4}$ and $R^{f4}$ independently represents $C_{1-8}$ alkyl, $C_{2-8}$ alkenyl or $C_{2-8}$ alkynyl each optionally substituted by one or more groups independently selected from $G^{4a}$, heterocyclyl optionally substituted by one or more groups independently selected from $G^{4b}$, aryl optionally substituted by one or more groups independently selected from $G^{4c}$, or heteroaryl optionally substituted by one or more groups independently selected from $G^{4d}$;

each $R^{b4}$, $R^{c4}$, $R^{d4}$, $R^{e4}$, $R^{g4}$, $R^{h4}$, $R^{i4}$, $R^{j4}$, $R^{k4}$, $R^{l4}$, $R^{m4}$, $R^{n4}$, $R^{o4}$, $R^{p4}$, $R^{q4}$, $R^{r4}$, $R^{s4}$, $R^{t4}$, $R^{u4}$, $R^{v4}$, $R^{w4}$ and $R^{x4}$ independently represents H or $C_{1-8}$ alkyl, $C_{2-8}$ alkenyl or $C_{2-8}$ alkynyl each optionally substituted by one or more groups independently selected from $G^{4a}$, heterocyclyl optionally substituted by one or more groups independently selected from $G^{4b}$, aryl optionally substituted by one or more groups independently selected from $G^{4c}$, or heteroaryl optionally substituted by one or more groups independently selected from $G^{4d}$, or alternatively any of $R^{c4}$ and $R^{d4}$, $R^{g4}$ and $R^{h4}$, $R^{j4}$ and $R^{k4}$, $R^{o4}$ and $R^{p4}$ and/or $R^{v4}$ and $R^{w4}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl, $C_{2-3}$ alkenyl or $C_{2-3}$ alkynyl each optionally substituted by one or more halo, and =O, or alternatively two $R^{n4}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halo, $C_{1-3}$alkyl optionally substituted by one or more halo, and =O, or alternatively two $R^{r4}$ are linked together to form, along with the phosphorus, and the oxygen atoms to which they are attached, a 5- to 8-membered heterocyclic ring, which ring optionally contains one or more further heteroatoms and which ring optionally is substituted by one or more groups independently selected from halo, $C_{1-3}$ alkyl optionally substituted by one or more halo, and =O;

each $G^{2a}$ independently represents halo, —CN, -A$^{a4}$-C(Q$^{a3}$)R$^{b5}$, A$^{b4}$-C(Q$^{c3}$)N(R$^{c5}$)R$^{d5}$, -A$^{c4}$-C(Q$^{c3}$)OR$^{e5}$, -A$^{d4}$-S(O)$_p$R$^{f5}$, -A$^{e4}$-S(O)$_p$N(R$^{g5}$)R$^{h5}$, -AM-S(O)$_p$OR$^{i5}$, —N$_3$, —N(R$^{j5}$)R$^{k5}$, —N(H)CN, —NO$_2$, —ONO$_2$, —OR$^{l5}$, —SR$^{m5}$—B(OR$^{n5}$)$_2$, —P(O)(N(R$^{o5}$)R$^{p5}$)$_2$, —P(O)(N(R$^{o5}$)R$^{p5}$)(OR$^{q5}$) or —P(O)(OR$^{r5}$)$_2$ or =Q$^{d3}$;

each $G^{2b}$ independently represents halo, R$^{a5}$, —CN, -A$^{a4}$-C(Q$^{a3}$)R$^{b5}$, -A$^{b4}$-C(Q$^{c3}$)N(R$^{c5}$)R$^{d5}$, -A$^{c4}$-C(Q$^{c3}$)OR$^{e5}$, -A$^{d4}$-S(O)$_p$R$^{f5}$, -A$^{e4}$-S(O)$_p$N(R$^{g5}$)R$^{h5}$, -A$^{f4}$-S(O)$_p$OR$^{i5}$, —N$_3$, —N(R$^{j5}$)R$^{k5}$, —N(H)CN, —NO$_2$, —ONO$_2$, —OR$^{l5}$, —SR$^{m5}$—B(OR$^{n5}$)$_2$, —P(O)(N(R$^{o5}$)R$^{p5}$)$_2$, —P(O)(N(R$^{o5}$)R$^{p5}$)(OR$^{q5}$) or —P(O)(OR$^{r5}$)$_2$ or =Q$^{d3}$;

each $A^{a4}$ to $A^{f4}$ independently represents a single bond, —C(O)N(R$^{s5}$)—, —N(R$^{t5}$)— or —O—;

each $Q^{a3}$ to $Q^{d3}$ independently represents =O, =S, =C(H)NO$_2$, =N(CN), =NR$^u$, =NN(R$^{v5}$)R$^{w5}$ or =N(OR$^{x5}$), =NS(O)$_p$N(R$^{v5}$)R$^{w5}$;

each $G^{3a}$ and $G^{3b}$ independently represents halo, R$^{a6}$, —CN, -A$^{a5}$-C(Q$^{a4}$)R$^{b6}$e, -A$^{b5}$-C(Q$^{b4}$)N(R$^{c6}$)R$^{d6}$, -A$^{c5}$-C(Q$^{c4}$)OR$^{e6}$, -A$^{d5}$-S(O)$_p$R$^{f6}$, -A$^{e5}$-S(O)$_p$N(R$^{g6}$)R$^{h6}$, -A$^{f5}$-S(O)$_p$OR$^{i6}$, —N$_3$, —N(R$^{j5}$)R$^{k6}$, —N(H)CN, —NO$_2$, —ONO$_2$, —OR$^{l6}$, —SR$^{m6}$—B(OR$^{n6}$)$_2$, —P(O)(N(R$^{o6}$)R$^{p6}$)$_2$, —P(O)(N(R$^{o6}$)RP)(OR$^{q6}$) or —P(O)(OR$^{r6}$)$_2$ or =Q$^{d4}$;

each $A^{a5}$ to $A^{f5}$ independently represents a single bond, —C(O)N(R$^{s6}$)—, —N(R$^{t6}$)— or —O—;

each $Q^{a4}$ to $Q^{d4}$ independently represents =O, =S, =C(H)NO$_2$, =N(CN), =NR$^{u6}$, =NN(R$^{v6}$)R$^{w6}$ or =N(OR$^{x6}$), =NS(O)$_p$N(R$^{v6}$)R$^{w6}$;

each $R^{a5}$ and $R^{f5}$ independently represents $C_{1-6}$ alkyl optionally substituted by one or more F;

each $R^{b5}$, $R^{c5}$, $R^{d5}$, $R^{e5}$, $R^{g5}$, $R^{h5}$, $R^{i5}$, $R^{j5}$, $R^{k5}$, $R^{l5}$, $R^{m5}$, $R^{n5}$, $R^{o5}$, $R^{p5}$, $R^{q5}$, $R^{r5}$, $R^{s5}$, $R^{t5}$, $R^{u5}$, $R^{v6}$, $R^{x6}$ and $R^{y6}$ independently represents H or $C_{1-6}$ alkyl optionally substituted by one or more F, or alternatively any of $R^{c5}$ and $R^{d5}$, $R^{g5}$ and $R^{h5}$, $R^{j5}$ and $R^{k5}$, $R^{o5}$ and $R^{p5}$ and/or $R^{v5}$ and $R^{w5}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $R^{a6}$ and $R^{f6}$ independently represents $C_{1-6}$ alkyl, $C_{2-6}$ alkenyl or $C_{2-6}$ alkynyl, each optionally substituted by one or more groups independently selected from $G^{5a}$, heterocyclyl optionally substituted by one or more groups independently selected from $G^{5b}$, aryl optionally substituted by one or more groups independently selected from $G^{5c}$, or heteroaryl optionally substituted by one or more groups independently selected from $G^{5d}$;

each $R^{b6}$, $R^{c6}$, $R^{d6}$, $R^{e6}$, $R^{g6}$, $R^{h6}$, $R^{i6}$, $R^{j6}$, $R^{k6}$, $R^{l6}$, $R^{m6}$, $R^{n6}$, $R^{o6}$, $R^{p6}$, $R^{q6}$, $R^{r6}$, $R^{s6}$, $R^{t6}$, $R^{u6}$, $R^{v6}$, $R^{w6}$ and $R^{x6}$, independently represents H or independently represents $C_{1-6}$ alkyl, $C_{2-6}$ alkenyl or $C_{2-6}$ alkynyl, each optionally substituted by one or more groups independently selected from $G^{5a}$, heterocyclyl optionally substituted by one or more groups independently selected from $G^{5b}$, aryl optionally substituted by one or more groups independently selected from $G^{5c}$, or heteroaryl optionally substituted by one or more groups independently selected from $G^{5d}$, or alternatively any of $R^{c6}$ and $R^{d6}$, $R^{g6}$ and $R^{h6}$, $R^{j6}$ and $R^{k6}$, $R^{o6}$ and $R^{p6}$ and/or $R^{v6}$ and $R^{w6}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $G^{4a}$, $G^{4b}$, $G^{4c}$ and $G^{4d}$ independently represents halo, R$^{a7}$, —CN, -A$^{a6}$C(Q$^{a5}$)R$^{b7}$, -A$^{b6}$-C(Q$^{b5}$)N(R$^{c7}$)R$^{d7}$, -A$^{c6}$-C(Q$^{c5}$)OR$^{e7}$, -A$^{d6}$-S(O)$_p$R$^{f7}$, -A$^{e6}$-S(O)$_p$N(R$^{g7}$)R$^{h7}$, -A$^{f6}$-S(O)$_p$OR$^{i7}$, —N$_3$, —N(R$^{j7}$)R$^{k7}$, —N(H)CN, —NO$_2$, —ONO$_2$, —OR$^{l7}$, —SR$^{m7}$—B(OR$^{n7}$)$_2$, —P(O)(N(R$^{o7}$)R$^{p7}$)$_2$, —P(O)(N(R$^{o7}$)R$^{p7}$)(OR$^{q7}$) or —P(O)(OR$^{r7}$)$_2$ or =Q$^{d5}$;

each $A^{a6}$ to $A^{f6}$ independently represents a single bond, —C(O)N(R$^{s7}$)—, —N(R$^{t7}$)— or —O—;

each $Q^{a5}$ to $Q^{d5}$ independently represents =O, =S, =C(H)NO$_2$, =N(CN), =NR$^{u7}$, =NN(R$^{v7}$)R$^{w7}$ or =N(OR$^{x7}$), =NS(O)$_p$N(R$^{v7}$)R$^{w7}$;

each $R^{a7}$ and $R^{f7}$ independently represents $C_{1-6}$ alkyl, $C_{2-6}$ alkenyl or $C_{2-6}$ alkynyl, each optionally substituted by one or more groups independently selected from $G^{6a}$, heterocyclyl optionally substituted by one or more groups independently selected from $G^{6b}$, aryl optionally substituted by one or more groups independently selected from $G^{6c}$, or heteroaryl optionally substituted by one or more groups independently selected from $G^{6d}$;

each $R^{b7}$, $R^{c7}$, $R^{d7}$, $R^{e7}$, $R^{g7}$, $R^{h7}$, $R^{i7}$, $R^{j7}$, $R^{k7}$, $R^{l7}$, $R^{m7}$, $R^{n7}$, $R^{o7}$, $R^{p7}$, $R^{q7}$, $R^{r7}$, $R^{s7}$, $R^{t7}$, $R^{u7}$, $R^{v7}$, $R^{w7}$ and $R^{x7}$ independently represents H or $C_{1-6}$ alkyl, $C_{2-6}$ alkenyl or $C_{2-6}$ alkynyl, each optionally substituted by one or more groups independently selected from $G^{6a}$, heterocyclyl optionally substituted by one or more groups independently selected from $G^{6b}$, aryl optionally substituted by one or more groups independently selected from $G^{6c}$, or heteroaryl optionally substituted by one or more groups independently selected from $G^{6d}$, or alternatively any of $R^{c7}$ and $R^{d7}$, $R^{g7}$ and $R^{h7}$, $R^{j7}$ and $R^{k7}$, $R^{n7}$ and $R^{o7}$ and/or $R^{v7}$ and $R^{w7}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $G^{5a}$, $G^{5b}$, $G^{5c}$ and $G^{5d}$ independently represents halo, $R^{a8}$, —CN, -$A^{a7}$-C($Q^{a6}$)$R^{b8}$, -$A^{b7}$-C($Q^{b6}$)N($R^{c8}$)$R^{d8}$, -$A^{c7}$-C($Q^{c6}$)O$R^{e8}$, -$A^{d7}$-S(O)$_p R^{f8}$, -$A^{e7}$-S(O)$_p$N($R^{g8}$)$R^{h8}$, -$A^{f7}$-S(O)$_p$O$R^{i8}$, —$N_3$, —N($R^{j8}$)$R^{k8}$, —N(H)CN, —NO$_2$, —ONO$_2$, —O$R^{l8}$, —S$R^{m8}$—B(O$R^{n8}$)$_2$, —P(O)(N($R^{o8}$)$R^{p8}$)$_2$, —P(O)(N($R^{o8}$)$R^{p8}$)(O$R^{q8}$) or —P(O)(O$R^{r8}$)$_2$ or =$Q^{d6}$;

each $A^{a7}$ to $A^{f7}$ independently represents a single bond, —C(O)N($R^{s8}$)—, —N($R^{t8}$)— or —O—;

each $Q^{a6}$ to $Q^{d6}$ independently represents =O, =S, =C(H)NO$_2$, =N(CN), =N$R^{u8}$, =NN($R^{v8}$)$R^{w8}$ or =N(O$R^{x8}$), =NS(O)$_p$N($R^{v8}$)$R^{w8}$;

each $G^{6a}$, $G^{6b}$, $G^{6c}$ and $G^{6d}$ independently represents halo, $R^{a9}$, —CN, -$A^{a8}$-C($Q^{a7}$)$R^{b9}$, -$A^{b8}$-C($Q^{b7}$)N($R^{c9}$)$R^{d9}$, -$A^{c8}$-C($Q^{c7}$)O$R^{e9}$, -$A^{d8}$-S(O)$_p R^{f9}$, -$A^{e8}$-S(O)$_p$N($R^{g9}$)$R^{h9}$, -$A^{f8}$-S(O)$_p$O$R^{i9}$, —$N_3$, —N($R^{j9}$)$R^{k9}$, —N(H)CN, —NO$_2$, —ONO$_2$, —O$R^{l9}$, —S$R^{m9}$—B(O$R^{n9}$)$_2$, —P(O)(N($R^{o9}$)$R^{p9}$)$_2$, —P(O)(N($R^{o9}$)$R^{p9}$)(O$R^{q9}$) or —P(O)(O$R^{r9}$)$_2$ or =$Q^{d7}$;

each $A^{a8}$ to $A^{f8}$ independently represents a single bond, —C(O)N($R^{s9}$)—, —N($R^{t9}$)— or —O—;

each $Q^{a7}$ to $Q^{d7}$ independently represents =O, =S, =C(H)NO$_2$, =N(CN), =N$R^{u9}$, =NN($R^{v9}$)$R^{w9}$ or =N(O$R^{x9}$), =NS(O)$_p$N($R^{v9}$)$R^{w9}$;

each $R^{a8}$ and $R^{f8}$ independently represents H or $C_{1-6}$ alkyl optionally substituted by one or more F;

each $R^{b8}$, $R^{c8}$, $R^{d8}$, $R^{e8}$, $R^{g8}$, $R^{h8}$, $R^{i8}$, $R^{j8}$, $R^{k8}$, $R^{l8}$, $R^{m8}$, $R^{n8}$, $R^{o8}$, $R^{p8}$, $R^{q8}$, $R^{r8}$, $R^{s8}$, $R^{t8}$, $R^{u8}$, $R^{v8}$, $R^{w8}$ and $R^{x8}$ independently represents H or $C_{1-6}$ alkyl optionally substituted by one or more F, or alternatively any of $R^{c8}$ and $R^{d8}$, $R^{g8}$ and $R^{h8}$, $R^{j8}$ and $R^{k8}$, $R^{n8}$ and $R^{o8}$ and/or $R^{v8}$ and $R^{w8}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $R^{a9}$ and $R^{f9}$ independently represents H or $C_{1-6}$ alkyl optionally substituted by one or more F;

each $R^{b9}$, $R^{c9}$, $R^{d9}$, $R^{e9}$, $R^{g9}$, $R^{h9}$, $R^{i9}$, $R^{j9}$, $R^{k9}$, $R^{l9}$, $R^{m9}$, $R^{n9}$, $R^{o9}$, $R^{p9}$, $R^{q9}$, $R^{r9}$, $R^{s9}$, $R^{t9}$, $R^{u9}$, $R^{v9}$, $R^{w9}$ and $R^{x9}$ independently represents H or $C_{1-6}$ alkyl optionally substituted by one or more F, or alternatively any of $R^{c9}$ and $R^{d9}$, $R^{g9}$ and $R^{h9}$, $R^{j9}$ and $R^{k9}$, $R^{n9}$ and $R^{o9}$ and/or $R^{v9}$ and $R^{w9}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O; and each p independently represents 1 or 2, which compounds may be referred to herein as the "compounds of the invention".

For the avoidance of doubt, the skilled person will understand that references herein to compounds of particular aspects of the invention (such as the first aspect of the invention, i.e. referring to compounds of formula I as defined in the first aspect of the invention) will include references to all embodiments and particular features thereof, which embodiments and particular features may be taken in combination to form further embodiments and features of the invention.

Unless indicated otherwise, all technical and scientific terms used herein will have their common meaning as understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention.

For the avoidance of doubt, compounds of the invention may also exist in solution (i.e. in solution in a suitable solvent). For example, compounds of the invention may exist in aqueous solution, in which case compounds of the invention may exist in the form of hydrates thereof.

Compounds of the invention (and similarly, compounds excluded from the scope of the invention) may contain double bonds and, unless otherwise indicated, may thus exist as E (entgegen) and Z (zusammen) geometric isomers about each individual double bond.

Unless otherwise specified, all such isomers and mixtures thereof are included within the scope of the invention (or within the relevant exclusion).

For the avoidance of doubt, where a bond is indicated by a wavy line (e.g. in the case of the bond to $R^1$ in formula I), the skilled person will understand that the substituent bond by that bond may be present in the E or Z configuration.

In particular embodiments of the first aspect of the invention (and all embodiments thereof), the bond to $R^1$ is present in the E configuration, as depicted for compounds of formula I below:

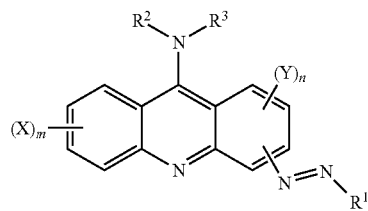

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques.

Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

For the avoidance of doubt, the skilled person will understand that where a particular group is depicted herein as being bound to a ring system via a floating bond (i.e. a bond not shown as being bound to a particular atom within the ring), the relevant group may be bound to any suitable atom within the relevant ring system (i.e. the ring within which the floating bond terminates).

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups.

Unless otherwise specified, $C_{2-z}$ alkenyl groups (where z is the upper limit of the range) defined herein may be straight-chain or, when there is a sufficient number (i.e. a minimum of three) of carbon atoms, be branched-chain, and/or cyclic (so forming a $C_{4-z}$ cycloalkenyl group). When there is a sufficient number (i.e. a minimum of five) of carbon atoms, such groups may also be part cyclic. For example, part cyclic alkenyl groups (which may also be referred to as "part cycloalkenyl" groups) that may be mentioned include cyclopentenylmethyl and cyclohexenylmethyl. When there is a sufficient number of carbon atoms, such groups may also be multicyclic (e.g. bicyclic or tricyclic) or spirocyclic. For the avoidance of doubt, particular alkenyl groups that may be mentioned include straight chain (i.e. not branched and/or cyclic) alkenyl groups.

Unless otherwise specified, $C_{2-z}$ alkynyl groups (where z is the upper limit of the range) defined herein may be straight-chain or, when there is a sufficient number (i.e. a minimum of four) of carbon atoms, be branched-chain. For the avoidance of doubt, particular alkynyl groups that may be mentioned include straight chain (i.e. not branched and/or cyclic) alkynyl groups.

For the avoidance of doubt, unless otherwise specified, groups referred to herein as "alkyl", "alkenyl" and/or "alkynyl" will be taken as referring to the highest degree of unsaturation in a bond present in such groups. For example, such a group having a carbon-carbon double bond and, in the same group, a carbon-carbon triple bond will be referred to as "alkynyl". Alternatively, it may be particularly specified that that such groups will comprise only the degree of unsaturation specified (i.e. in one or more bond therein, as appropriate; e.g. in in one bond therein).

For the avoidance of doubt, alkyl, alkenyl and alkynyl groups as described herein may also act as linker groups (i.e. groups joining two or more parts of the compound as described), in which case such groups may be referred to as "alkylene", "alkenylene" and/or "alkynylene" groups, respectively.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulfur (e.g. oxygen, nitrogen and sulfur, such as oxygen and nitrogen).

As used herein, the term heterocyclyl may refer to non-aromatic monocyclic and polycyclic (e.g. bicyclic) heterocyclic groups (which groups may, where containing a sufficient number of atoms, also be bridged) in which at least one (e.g. one to four) of the atoms in the ring system is other than carbon (i.e. a heteroatom), and in which the total number of atoms in the ring system is between three and twelve (e.g. between five and ten, such as between three and eight; for example, forming a 5- or 6-membered heterocyclyl group). Further, such heterocyclyl groups may be saturated, forming a heterocycloalkyl, or unsaturated containing one or more carbon-carbon or, where possible, carbon-heteroatom or heteroatom-heteroatom double and/or triple bonds, forming for example a $C_{2-z}$ (e.g. $C_{4-z}$) heterocycloalkenyl (where z is the upper limit of the range) or a $C_{7-z}$ heterocycloalkynyl group.

For the avoidance of doubt, the skilled person will understand that heterocyclyl groups that may form part of compounds of the invention are those that are chemically obtainable, as known to those skilled in the art. Various heterocyclyl groups will be well-known to those skilled in the art, such as 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridinyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), hexahydro-1H-thieno[3,4-d]imidazole, imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridinyl (such as 1,2,3,4-tetrahydropyridinyl and 1,2,3,6-tetrahydropyridinyl), thietanyl, thiiranyl, thiolanyl, tetrahydrothiopyranyl, thiomorpholinyl, trithianyl (including 1,3,5-trithianyl), tropanyl and the like.

Substituents on heterocyclyl groups may, where appropriate, be located on any atom in the ring system including a heteroatom. Further, in the case where the substituent is another cyclic compound, then the cyclic compound may be attached through a single atom on the heterocyclyl group, forming a spirocyclic compound. The point of attachment of heterocyclyl groups may be via any suitable atom in the ring system, including (where appropriate) a further heteroatom (such as a nitrogen atom), or an atom on any fused carbocyclic ring that may be present as part of the ring system. Heterocyclyl groups may also be in the N- or S-oxidised forms, as known to those skilled in the art.

At each occurrence when mentioned herein, particular heterocyclyl groups that may be mentioned include 3- to 8-membered heterocyclyl groups (e.g. a 4- to 6-membered heterocyclyl group, such as a 5- or 6-membered heterocyclyl group). Certain heterocyclyl groups that may be mentioned include hexahydro-1H-thieno[3,4-d]imidazole (particularly the (3aR,6aS)-hexahydro-1H-thieno[3,4-d]imidazole isomer thereof).

For the avoidance of doubt, references to polycyclic (e.g. bicyclic or tricyclic) groups (for example when employed in the context of heterocyclyl or cycloalkyl groups (e.g. heterocyclyl)) will refer to ring systems wherein at least two scissions would be required to convert such rings into a non-cyclic (i.e. straight or branched) chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, to groups in which two non-adjacent atoms are linked by an alkyl (which, when linking two moieties, may be referred to as alkylene) group (optionally containing one or more heteroatoms), which later groups may be referred to as bridged, or to groups in which the second ring is attached to a single atom, which latter groups may be referred to as spiro compounds.

As may be used herein, the term aryl may refer to $C_{6-14}$ (e.g. $C_6$-10) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl, and the like). For the avoidance of doubt, the point of attachment of substituents on aryl groups may be via any suitable carbon atom of the ring system.

For the avoidance of doubt, the skilled person will understand that aryl groups that may form part of compounds of the invention are those that are chemically obtainable, as known to those skilled in the art. Particular aryl groups that may be mentioned include phenyl and naphthyl, such as phenyl.

As may be used herein, references to heteroaryl (with may also be referred to as heteroaromatic) groups may refer to 5- to 14- (e.g. 5- to 10-) membered heteroaromatic groups containing one or more heteroatoms (such as one or more heteroatoms selected from oxygen, nitrogen and/or sulfur). Such heteroaryl groups may comprise one, two, or three rings, of which at least one is aromatic. Substituents on heteroaryl/heteroaromatic groups may, where appropriate, be located on any suitable atom in the ring system, including a heteroatom (e.g. on a suitable N atom).

The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocyclyl ring.

For the avoidance of doubt, the skilled person will understand that heteroaryl groups that may form part of compounds of the invention are those that are chemically obtainable, as known to those skilled in the art. Various heteroaryl groups will be well-known to those skilled in the art, such as pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl.

For the avoidance of doubt, the oxides of heteroaryl/heteroaromatic groups are also embraced within the scope of the invention (e.g. the N-oxide).

As stated above, heteroaryl includes polycyclic (e.g. bicyclic) groups in which one ring is aromatic (and the other may or may not be aromatic). Hence, other heteroaryl groups that may be mentioned include groups such as benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl and the like.

Particular heteroaryl groups that may be mentioned include pyridinyl (e.g. pyridin-3-yl).

For the avoidance of doubt, where a ring is depicted having circle therein, its presence shall indicate that the relevant ring is aromatic. Alternatively, aromatic groups may be depicted as cyclic groups comprising therein a suitable number of double bonds to allow for aromaticity.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature).

All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more $R^{a2}$ groups are present, those $R^{a2}$ groups may be the same or different. Similarly, where two or more $R^{a2}$ groups are present and each represent $C_{1-12}$ alkyl, the $C_{1-12}$ alkyl groups in question (and any substituents thereon) may be the same or different. Also for the avoidance of doubt, when a term such as "$Q^{a1}$ to $Q^{c1}$" is employed herein, this will be understood by the skilled person to mean $Q^{a1}$, $Q^{b1}$ and $Q^{c1}$, inclusively. Unless otherwise stated, the same reasoning will apply to other such terms used herein.

Further for the avoidance of doubt, when it is specified that a substituent is itself optionally substituted by one or more substituents (e.g. $R^1$ represents $C_{1-12}$ alkyl optionally substituted by one or more groups independently selected from $G^a$), these substituents where possible may be positioned on the same or different atoms. Such optional substituents may be present in any suitable number thereof (e.g. the relevant group may be substituted with one or more such substituents, such as one such substituent).

For the avoidance of doubt, where groups are referred to herein as being optionally substituted it is specifically contemplated that such optional substituents may be not present (i.e. references to such optional substituents may be removed), in which case the optionally substituted group may be referred to as being unsubstituted.

Where used herein, a dashed bond (i.e. " - - - ", or the like) may indicate the position of attachment of the relevant substituent to the core molecule (i.e. the compound of the compound of formula I to which the substituent is attached).

For the avoidance of doubt, the skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

In a particular embodiment of the first aspect of the invention, there is the proviso that the following compounds are excluded:
6-((4-(dimethylamino)phenyl)diazenyl)-2-ethoxyacridin-9-amine;
6,6'-(diazene-1,2-diyl)bis(2-ethoxyacridin-9-amine);
6-((1H-indol-2-yl)diazenyl)-2-ethoxyacridin-9-amine;
2-((9-amino-7-ethoxyacridin-3-yl)diazenyl)-4-((diethylamino)methyl)-3,6-dimethylphenol;
$N^4$-(7-chloro-2-methoxy-3-(naphthalen-1-yldiazenyl)acridin-9-yl)-N,N'-diethylpentane-1,4-diamine;
(E)-$N^4$-(7-chloro-2-methoxy-3-(naphthalen-1-yldiazenyl)acridin-9-yl)-N,N'-diethylpentane-1,4-diamine;
3-((9-amino-6-ethoxyacridin-3-yl)diazenyl)pyridine-2,6-diamine;
3-((9-amino-7-ethoxyacridin-3-yl)diazenyl)pyridine-2,6-diamine;
4-amino-2-((9-amino-7-ethoxyacridin-3-yl)diazenyl)naphthalene-1-sulfonic acid;
4-((9-amino-7-ethoxyacridin-3-yl)diazenyl)-2,5-dimethylphenol;
4-((9-amino-7-ethoxyacridin-3-yl)diazenyl)-2,6-dimethylphenol; and
4-amino-N-(5-((9-amino-7-ethoxyacridin-3-yl)diazenyl)thiazol-2-yl)benzenesulfonamide,
and optionally pharmaceutically acceptable salts thereof.

In more particular embodiments (i.e. more particular embodiments of the first aspect of the invention), the compound of formula I is not a compound selected from the list consisting of:
6-((4-(dimethylamino)phenyl)diazenyl)-2-ethoxyacridin-9-amine;
6,6'-(diazene-1,2-diyl)bis(2-ethoxyacridin-9-amine);
6-((1H-indol-2-yl)diazenyl)-2-ethoxyacridin-9-amine;
2-((9-amino-7-ethoxyacridin-3-yl)diazenyl)-4-((diethylamino)methyl)-3,6-dimethylphenol;
$N^4$-(7-chloro-2-methoxy-3-(naphthalen-1-yldiazenyl)acridin-9-yl)-N,N'-diethylpentane-1,4-diamine;
(E)-$N^4$-(7-chloro-2-methoxy-3-(naphthalen-1-yldiazenyl)acridin-9-yl)-N,N'-diethylpentane-1,4-diamine;
3-((9-amino-6-ethoxyacridin-3-yl)diazenyl)pyridine-2,6-diamine;
3-((9-amino-7-ethoxyacridin-3-yl)diazenyl)pyridine-2,6-diamine;
4-amino-2-((9-amino-7-ethoxyacridin-3-yl)diazenyl)naphthalene-1-sulfonic acid;
4-((9-amino-7-ethoxyacridin-3-yl)diazenyl)-2,5-dimethylphenol
4-((9-amino-7-ethoxyacridin-3-yl)diazenyl)-2,6-dimethylphenol; and
4-amino-N-(5-((9-amino-7-ethoxyacridin-3-yl)diazenyl)thiazol-2-yl)benzenesulfonamide.

In a particular embodiment of the first aspect of the invention, there is the proviso that the following compounds are also excluded:
6-((2-(dimethylamino)phenyl)diazenyl)-2-ethoxyacridin-9-amine;
6-((2-(diethylamino)phenyl)diazenyl)-2-ethoxyacridin-9-amine; and
2-(9-amino-5-ethoxy-2-acridinyl)diazenyl)-naphthylene-2-yl;
and
7-ethyoxy-4-(2-(4-nitrophenyl)diazenyl)-acridin-3,9-diamine;
and
N9-(2,2-dimethoxyethyl)-7-ethoxy-4-(2-(4-nitrophenyl)-diazenyl)-acridin-3,9-diamine;
and
4-amino-3-(2-(6-chloro-9-((4-diethylamino)-1-methylbutyl))amino)-2-acridinyl)-diazenyl-naphthalene-1-sulfonic acid; and
1-(2-(6-chloro-9-((4-diethylamino)-1-methylbutyl))amino)amino-2-acridinyl)-diazenyl-naphthalen-2-ol;
and
2,2'-(1,2-diazenediylbis(1,9-acridinediylimino))bis-ethanol;
2,2'-(1,2-diazenediylbis(4-methyl-1,9-acridinediylimino))bis-ethanol;
and 4-amino-N-(5-(2-(9-amino-7-ethyoxy-3-acridinyl)diaz-enyl)-4-methyl-2-thiazolyl)-benzenesulfonamide,
and optionally pharmaceutically acceptable salts thereof.

In yet more particular embodiments (i.e. more particular embodiments of the first aspect of the invention), the compound of formula I is also not a compound selected from the list consisting of:
6-((2-(dimethylamino)phenyl)diazenyl)-2-ethoxyacridin-9-amine;
6-((2-(diethylamino)phenyl)diazenyl)-2-ethoxyacridin-9-amine; and
2-(9-amino-5-ethoxy-2-acridinyl)diazenyl)-naphthylene-2-yl;
and
7-ethyoxy-4-(2-(4-nitrophenyl)diazenyl)-acridin-3,9-diamine;
and
N9-(2,2-dimethoxyethyl)-7-ethoxy-4-(2-(4-nitrophenyl)-diazenyl)-acridin-3,9-diamine;
and
4-amino-3-(2-(6-chloro-9-((4-diethylamino)-1-methyl-butyl))amino)-2-acridinyl)-diazenyl-naphthalene-1-sulfonic acid; and
1-(2-(6-chloro-9-((4-diethylamino)-1-methylbutyl))amino) amino-2-acridinyl)-diazenyl-naphthalen-2-ol;
and
2,2'-(1,2-diazenediylbis(1,9-acridinediylimino))bis-ethanol;
2,2'-(1,2-diazenediylbis(4-methyl-1,9-acridinediylimino)) bis-ethanol;
and
4-amino-N-(5-(2-(9-amino-7-ethyoxy-3-acridinyl)diaz-enyl)-4-methyl-2-thiazolyl)-benzenesulfonamide.

In particular embodiments (i.e. particular embodiments of the first aspect of the invention), the compound of formula I is such that:
$R^1$ represents aryl optionally substituted by one or more groups independently selected from $G^{1c}$, or heteroaryl optionally substituted by one or more groups independently selected from $G^{1d}$.

In more particular embodiments, the compound of formula I is such that: $R^1$ represents phenyl optionally substituted by one or more groups independently selected from $G^{1c}$, or a 6-membered heteroaryl optionally substituted by one or more groups independently selected from $G^{1d}$.

In yet more particular embodiments, the compound of formula I is such that:
$R^1$ represents phenyl optionally substituted by one or more (e.g. one, two or three, such as two or three) groups independently selected from $G^{1c}$, or pyridinyl (e.g. pyridine-3-yl) optionally substituted by one or more (e.g. one or two, such as two) groups independently selected from $G^{1d}$.

In certain embodiments, the compound of formula I is such that $R^1$ represents aryl optionally substituted by one or more (e.g. one, two or three, such as two or three) groups independently selected from $G^{1c}$.

In further embodiments, the compound of formula I is such that $R^1$ represents phenyl optionally substituted by one or more (e.g. one, two or three, such as two or three) groups independently selected from $G^{1c}$.

In alternative embodiments that may be mentioned: each $R^{b4}$, $R^{c4}$, $R^{d4}$, $R^{e4}$, $R^{g4}$, $R^{h4}$, $R^{i4}$, $R^{j4}$, $R^{k4}$, $R^{l4}$, $R^{m4}$, $R^{n4}$, $R^{o4}$, $R^{p4}$, $R^{q4}$, $R^{r4}$, $R^{s4}$, $R^{t4}$, $R^{u4}$, $R^{v4}$, $R^{w4}$ and $R^{x4}$ independently represents $C_{1-8}$ alkyl, $C_{2-8}$ alkenyl or $C_{2-8}$ alkynyl each optionally substituted by one or more groups independently selected from $G^{4a}$, heterocyclyl optionally substituted by one or more groups independently selected from $G^{4b}$, aryl optionally substituted by one or more groups independently selected from $G^{4c}$, or heteroaryl optionally substituted by one or more groups independently selected from $G^{4d}$, or alternatively any of $R^{c4}$ and $R^{d4}$, $R^{g4}$ and $R^{h4}$, $R^{j4}$ and $R^{k4}$, $R^{o4}$ and $R^{p4}$ and/or $R^{v4}$ and $R^{w4}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl, $C_{2-3}$ alkenyl or $C_{2-3}$ alkynyl each optionally substituted by one or more halo, and =O, or alternatively two $R^{n4}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halo, $C_{1-3}$alkyl optionally substituted by one or more halo, and =O, or alternatively two $R^{r4}$ are linked together to form, along with the phosphorus, and the oxygen atoms to which they are attached, a 5- to 8-membered heterocyclic ring, which ring optionally contains one or more further heteroatoms and which ring optionally is substituted by one or more groups independently selected from halo, $C_{1-3}$ alkyl optionally substituted by one or more halo, and =O.

In particular embodiments, each $G^{1c}$ and $G^{1d}$ independently represents halo (e.g. fluoro), $R^{a4}$, —N($R^{j4}$)$R^{k4}$ or —OR$^{l4}$, particularly wherein $R^{a4}$ represents $C_{1-12}$ alkyl optionally substituted by one or more groups independently selected from $G^{4a}$ (such as wherein $G^{4a}$ represents fluoro).

In particular embodiments, each $G^{1c}$ and $G^{1d}$ independently represents $C_{1-12}$ alkyl optionally substituted by one or more groups independently selected from $G^{4a}$ (such as wherein $G^{4a}$ represents fluoro), —N($R^{j4}$)$R^{k4}$ or —OR$^{l4}$, particularly wherein $R^{j4}$, $R^{k}4$ and $R^{l4}$ represent H.

In more particular embodiments, each $G^{1c}$ and $G^{1d}$ independently represents $C_{1-3}$ alkyl (e.g. $C_1$ alkyl, i.e. methyl) optionally substituted by one or more groups independently selected from $G^{4a}$ (such as wherein $G^{4a}$ represents fluoro), —N($R^{j4}$)$R^{k4}$ or —OR$^{l4}$, particularly wherein $R^{j4}$, $R^{k}4$ and $R^{l4}$ represent H.

In alternative embodiments, particularly wherein $R^1$ represents aryl optionally substituted by one or more (e.g. two) groups independently selected from $G^{1c}$, each $G^{1c}$ group independently represents —OH or $C_{1-3}$ alkyl (e.g. $C_1$ alkyl, i.e. methyl) optionally substituted by one or more groups independently selected from $G^{4a}$; for example, wherein one $G^{1c}$ group i represents —OH (e.g. in the position para to the point of attachment to the essential diazenyl moiety) or and the other represents $C_{1-3}$ alkyl (e.g. $C_1$ alkyl, i.e. methyl; e.g. in the corresponding meta position) optionally substituted by one or more groups independently selected from $G^{4a}$.

In certain embodiments, $G^{4a}$ represents halo (e.g. fluoro), —CN, —N($R^{j7}$)$R^{k7}$, —OR$^{l7}$, —SR$^{m7}$ or =$Q^{d5}$ (such as wherein $Q^{d5}$ represents O).

In further embodiments, $G^{4a}$ represents fluoro, —N($R^{j7}$)$R^{k7}$, —OR$^{l7}$ or =O.

In yet further embodiments, $G^{4a}$ represents fluoro, —N($R^{j7}$)$R^{k7}$ or —OR$^{l7}$ (e.g. —N($R^{j7}$)$R^{k7}$ or —OR$^{l7}$).

In certain embodiments, each $R^{j7}$, $R^{k7}$ and $R^{l7}$ independently represents H or $C_{1-6}$ alkyl (e.g. $C_{1-5}$ alkyl) optionally substituted by one or more groups independently selected from G, such as wherein each $G^{6a}$ independently represents halo (e.g. fluoro), $R^{a9}$, —CN, —N($R^{j9}$)$R^{k9}$, —OR$^{l9}$, —SR$^{m9}$ or =$Q^{d7}$ (such as wherein $Q^{d7}$ represents O).

In further embodiments, each $R^{j71}$, $R^{k7}$ and $R^{l7}$ independently represents H or $C_{1-6}$ alkyl (e.g. $C_{1-5}$ alkyl) optionally substituted by one or more groups independently selected from G, such as wherein each $G^{6a}$ independently represents —N(R$^9$)R$^{k9}$, —OR$^{j9}$ or =O.

In yet further embodiments, each R$^{j7}$, R$^{k7}$ and R$^{l7}$ independently represents H or C$_{1-6}$ alkyl (e.g. C$_{1-5}$ alkyl) optionally substituted by one or more groups independently selected from G$^{6a}$, such as wherein each G$^{6a}$ independently represents —N(R$^{j9}$)R$^{k9}$ or =O.

In certain embodiments, each R$^{j9}$, R$^{k9}$ and R$^{l9}$ (or R$^{j9}$ and R$^{k9}$) independently represents H or C$_{1-3}$ alkyl optionally substituted by one or more F.

In further embodiments, each R$^{j9}$, R$^{k9}$ and R$^{l9}$ (or R$^{j9}$ and R$^{k9}$) independently represents methyl.

In yet more particular embodiments, each G$^{1c}$ and G$^{1d}$ independently represents C$_1$ alkyl (i.e. methyl) optionally substituted by one or more fluoro, —NH$_2$ or —OH.

Particular R$^1$ groups that may be mentioned include those depicted below:

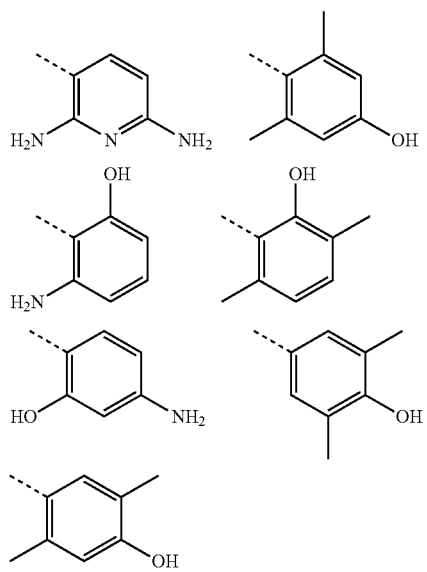

wherein, for the avoidance of doubt, the dashed bond indicates the point of attachment. Other R$^1$ groups that may be mentioned include those depicted below:

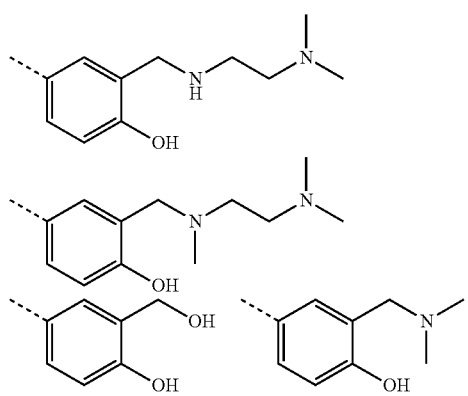

Where compounds of the invention comprise a detectable label, further R$^1$ groups that may be mentioned include those depicted below:

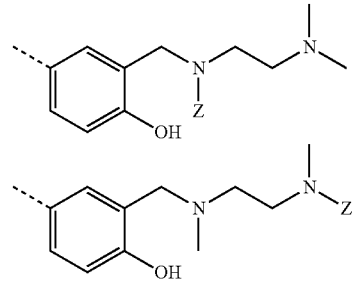

wherein Z represents a detectable group (i.e. a detectable label; e.g. as defined herein below).

In alternative embodiments that may be mentioned:
each R$^{b7}$, R$^{c7}$, R$^{d7}$, R$^{e7}$, R$^{g7}$, R$^{h7}$, R$^{i7}$, R$^{j7}$, R$^{k7}$, R$^{l7}$, R$^{m7}$, R$^{n7}$, R$^{o7}$, R$^{p7}$, R$^{q7}$, R$^{r7}$, R$^{s7}$, R$^{t7}$, R$^{u7}$, R$^{v7}$, R$^{w7}$ and R$^{x7}$ independently represents C$_{1-6}$ alkyl, C$_{2-6}$ alkenyl or C$_{2-6}$ alkynyl, each optionally substituted by one or more groups independently selected from G$^{6a}$, heterocyclyl optionally substituted by one or more groups independently selected from G$^{6b}$, aryl optionally substituted by one or more groups independently selected from G$^{6c}$, or heteroaryl optionally substituted by one or more groups independently selected from G$^{6d}$, or alternatively
any of R$^{c7}$ and R$^{d7}$, R$^{g7}$ and R$^{h7}$, R$^{j7}$ and R$^{k7}$, R$^{n7}$ and R$^{o7}$ and/or R$^{v7}$ and R$^{w7}$, are linked together to form, together with the nitrogen atom to which they are attached, a 3- to 6-membered ring, which ring optionally contains one further heteroatom and which ring optionally is substituted by one or more groups independently selected from F, C$_{1-3}$ alkyl optionally substituted by one or more F, and =O.

In particular embodiments, the compound of formula I is a compound of formula Ia

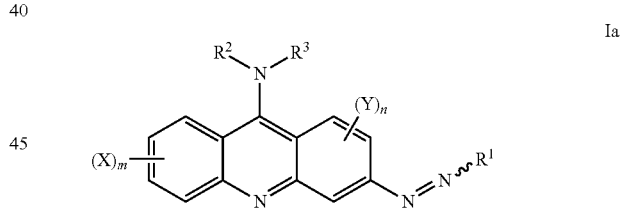

wherein R$^1$ to R$^3$, X, Y, m and n are as defined for compounds of formula I (including all embodiments thereof).

In more particular embodiments, the compound of formula I is a compound of formula Ia'

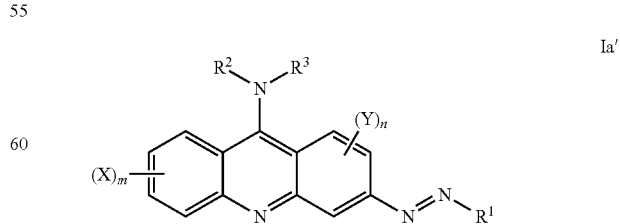

wherein R$^1$ to R$^3$, X, Y, m and n are as defined for compounds of formula I (including all embodiments thereof).

In particular embodiments, n represents 0 (i.e. there is no Y substituent present).

In particular embodiments, $R^3$ represents H.

In particular embodiments, $R^2$ and $R^3$ each represent H.

In certain embodiments, m represents 0 or 1.

In particular embodiments, m represents at least 1 (i.e. at least one X substituent is present), such as wherein m represents 1. In such embodiments, the essential X group may be present in the 7-position of the acridine ring (with m−1, which may be referred to as t, indicating the number of remaining X group(s) that is/are optionally present in other positions). For example, in relation to compounds of formula Ia and Ia' wherein the essential diazinyl group in the 3-position, at least one X group may be present in the 7-position.

In particular embodiments, the compound of formula I is a compound of formula Ib

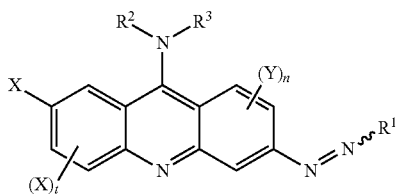

Ib wherein $R^1$ to $R^3$, X, Y and n are as defined for compounds of formula I (including all embodiments thereof) and t represents 0, 1, 2 or 3.

In more particular embodiments, the compound of formula I is a compound of formula Ib'

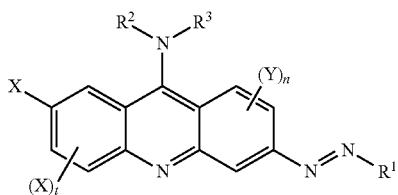

Ib' wherein $R^1$ to $R^3$, X, Y and n are as defined for compounds of formula I (including all embodiments thereof) and t represents 0, 1, 2 or 3.

In particular embodiments, t represents 0.

In particular embodiments, n represents 0.

Thus, in particular embodiments that may be mentioned, m represents 1 (or t represents 0) and n represents 0.

For example, in particular embodiments the compound of formula I is a compound of formula Ic

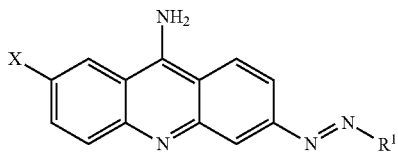

Ic wherein $R^1$ and X are as defined for compounds of formula I (including all embodiments thereof).

In particular embodiments, each X independently represents halo (e.g. fluoro or chloro, such as fluoro) or —$OR^{12}$.

In certain embodiments, at least one X (e.g. where defined, the essential X substituent) represents —$OR^{12}$, and any remaining X groups, if present, represent fluoro or chloro (e.g. fluoro).

In particular embodiments:
t represents 0; and/or (e.g. and)
X represents —$OR^{12}$.

Thus, in particular embodiments the compound of formula I is a compound of formula Id

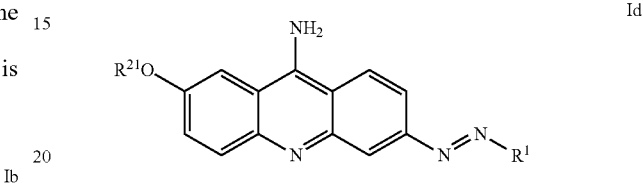

Id wherein $R^1$ and $R^{21}$ are defined for compounds of formula I (including all embodiments thereof).

In particular embodiments, each $R^{12}$ represents $C_{1-12}$ alkyl optionally substituted by one or more groups independently selected from $G^{3a}$ (such as wherein $G^{3a}$ represents fluoro).

In more particular embodiments, each $R^{12}$ represents $C_{1-6}$ alkyl optionally substituted by one or more groups independently selected from $G^{3a}$ (such as wherein $G^{3a}$ represents fluoro).

In yet more particular embodiments, each $R^{12}$ represents $C_{1-3}$ alkyl (e.g. $C_2$ alkyl, i.e. ethyl) optionally substituted by one or more groups independently selected from $G^{3a}$ (such as wherein $G^{3a}$ represents fluoro).

Thus, in more particular embodiments, each $R^{12}$ represents $C_2$ alkyl optionally substituted by one or more fluoro.

As described herein, in the first aspect of the invention there is provided a compound of formula I (including all embodiments thereof, such as compounds of formula Ia, Ia', Ib, Ib', Ic and Id) or a pharmaceutically-acceptable salt and/or detectably-labelled derivative thereof.

For the avoidance of doubt, where compounds of the invention are present detectably-labelled derivative thereof, such derivatives may also be in the form of a pharmaceutically-acceptable salt.

In particular embodiments, the compound of the invention is a compound of formula I or a pharmaceutically-acceptable salt thereof.

In alternative embodiments, the compound of the invention is a detectably-labelled derivative of a compound of formula I, or a pharmaceutically-acceptable salt thereof.

The skilled person will be aware of numerous means for preparing detectably-labelled derivatives of compounds as described herein. For example, where the compound of the invention is detectably-labelled derivative of a compound of formula I, or a pharmaceutically-acceptable salt thereof, the compound of formula I as defined may be further substituted by (i.e. a H group as present in such compounds may be replaced with) one or more (e.g. one) additional substituent forming a detectable label.

In particular embodiments, the one or more detectable label will be present as a substituent on a heteroatom, which heteroatom may be present in formula I (including all embodiments thereof) or as part of a substituent as defined for formula I, such as by replacing a H on a hydroxy or amine group.

In particular, such detectable labels may be present as alternative groups representing: an $R^2$ and/or (e.g. or) $R^3$ substituent;
one or more (e.g. one) substituents on $R^1$, e.g. as, or as a part of, a $G^{1a}$, $G^{1b}$, $G^{1c}$ and/or (e.g. or) $G^{1d}$ group;
one or more (e.g. one) substituent(s) representing an X group, e.g. as part of $R^{a2}$, $-A^{a1}-C(Q^{a1})R^{b2}$, $-A^{b1}-C(Q^{b1})N(R^{c2})R^{d2}$, $-A^{c1}-C(Q^{c1})OR^{e2}$, $-A^{d1}-S(O)_pR^{f2}$, $-A^{e1}-S(O)_pN(R^{g2})R^{h2}$, $-A^{f1}-S(O)_pOR^{i2}$, $-N(R^{j2})R^{k2}$, $-OR^{l2}$, $-SR^{m2}$, $-B(OR^{n2})_2$, $-P(O)(N(R^{o2})R^{p2})_2$, $-P(O)(N(R^{o2})R^{p2})(OR^{q2})$ or $-P(O)(OR^{r2})_2$ groups; and/or (e.g. or) one or more (e.g. one) substituent(s) representing a Y group, e.g. as, or as a part of, $R^{a3}$, $-A^{a2}-C(O)R^{b3}$, $-A^{b2}-C(O)N(R^{c3})R^{d3}$, $-A^{c2}-C(O)OR^{e3}$, $-A^{d2}-S(O)_pR^3$, $-A^{e2}-S(O)_pN(R^{g3})R^{h3}$, $-A^{f2}-S(O)_pOR^{i3}$, $-N(R^{j3})R^{k3}$, $-OR^{l3}$ or $-SR^{m3}$.

In particular embodiments, the detectable label may be present as an alternative group representing:
$G^{1a}$ (or as part of a $G^{1a}$ group, e.g. as a $R^{b4}$, $R^{c4}$, $R^{d4}$, $R^{e4}$, $R^{f4}$, $R^{g4}$, $R^{h4}$, $R^{i4}$, $R^{j4}$, $R^{k4}$, $R^{l4}$, $R^{m4}$, $R^{n4}$, $R^{o4}$, $R^{p4}$, $R^{q4}$ or $R^{r4}$ group); or
$G^{1b}$, $G^{1c}$ or $G^{1d}$ (or as part of a $G^{1b}$, $G^{1c}$ or $G^{1d}$ group, e.g. as a $R^{b4}$, $R^{c4}$, $R^{d4}$, $R^{e4}$, $R^{f4}$, $R^{g4}$, $R^{h4}$, $R^{i4}$, $R^{j4}$, $R^{k4}$, $R^{l4}$, $R^{m4}$, $R^{n4}$, $R^{o4}$, $R^{p4}$, $R^{q4}$ or $R^{r4}$ group); or
$R^2$ or $R^3$; or
X, or as $G^{3a}$, $G^{3b}$, $R^{b2}$, $R^{c2}$, $R^{d2}$, $R^{e2}$, $R^{f2}$, $R^{g2}$, $R^{h2}$, $R^{i2}$, $R^{j2}$, $R^{k2}$, $R^{l2}$, $R^{m2}$, $R^{n2}$, $R^{o2}$, $R^{p2}$, $R^{q2}$ or $R^{r2}$; or
Y, or as $R^{b3}$, $R^{c3}$, $R^{d3}$, $R^{e3}$, $R^{f3}$, $R^{g3}$, $R^{h3}$, $R^{i3}$, $R^{j3}$, $R^{k3}$, $R^{l3}$ or $R^{m3}$.

For example, the detectable label may be present as an alternative group representing, at each instance, one or more (e.g. one) of:
$R^{j2}$, $R^{k2}$, $R^{l2}$ and $R^{m2}$;
$R^{j3}$, $R^{k3}$, $R^{l3}$ and $R^{m3}$; and
$R^{j4}$, $R^{k4}$, $R^{l4}$ and $R^{m4}$.

For the avoidance of doubt, in particular embodiments there is only one detectable label present in compounds of the invention (e.g. in particular embodiments, one of the above-mentioned groups may alternatively represent a detectable label).

Particular detectable labels that may be mentioned include those allowing for biotinylation of the compound of formula I (including all embodiments thereof), or pharmaceutically acceptable salt thereof, either directly (i.e. through direct substitution of the compound, such as by formation of an acid or amide with the carboxylic acid group of biotin), or via a linker group (which linker group may act as a substituent of the compound and be also bound to biotin via the carboxylic acid, such as through formation of an ester or amide thereof).

Further detectable groups (e.g. detectable labels) that may be mentioned include photoaffinity labels (PALs), such as azide groups.

Thus, in particular embodiments, the detectable label may be of formula -L-Z, wherein L represents either a direct bond or a suitable linker group and Z represents a detectable group.

The skilled person will understand that the term "detectable group", as used herein, will refer to a chemical moiety the presence of which may be identified, and the quantity and, in certain instances, distribution thereof measured, using assays as known to those skilled in the art.

In particular embodiments, the detectable group is biotin, or an ester or amide derivative thereof (i.e. an ester or amide formed with the biotin carboxylic acid group).

For the avoidance of doubt, the structure of biotin is as indicated below:

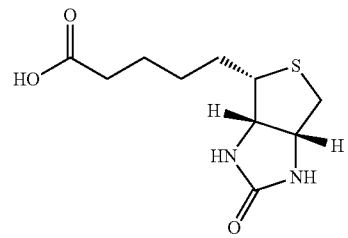 [SMILES: O=C(O)CCCC[C@@H]1SC[C@@H]2NC(=O)N[C@@H]21]

Thus, in particular embodiments Z (i.e. the detectable group) is of the following formula:

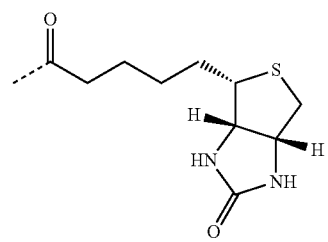

In particular embodiments, the detectable label is of the following formula:

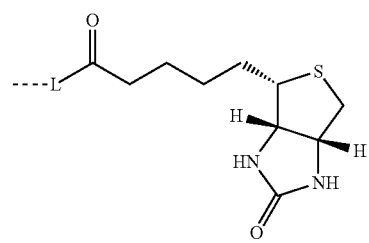

wherein L represents a direct bond or a suitable linker group.

In particular embodiments, L is a group of formula $-(R^{a10}-W^1)_v-$, wherein:
each $R^{a10}$ independently represents $C_{1-6}$ alkylene optionally substituted with one or more $R^{b10}$.
W represents $-O-$ or $-N(R^{c10})-$;
each $R^{b10}$ represents fluoro;
each $R^{c10}$ independently represents H or $C_{1-3}$ alkyl optionally substituted with one or more fluoro;
v represents 1 to 6.

Thus, in particular embodiments the detectable label is of the following formula:

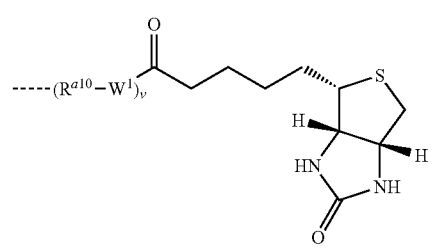

wherein $R^{a10}$, $W^1$ and v are as defined herein.

In particular embodiments, each $R^{a10}$ represents $C_{1-3}$ alkylene, such as n-propylene.

In particular embodiments, each $R^{c10}$ represents H.

In particular embodiments, at the point of attachment to Z, the relevant $W^1$ represents —$NR^{c10}$—, such as —NH—.

In alternative embodiments, L represents -$L^1$-$L^2$- (wherein $L^1$ forms the point of attachment to the compound of formula I), wherein:

$L^1$ represents —O— or —$NR^{d10}$—;
$L^2$ represents a group as defined herein for L; and
$R^{d10}$ represents $C_{1-3}$ alkyl (e.g. methyl) optionally substituted with one or more fluoro.

In alternative embodiments, Z may be represented by -$L^3$-$L^4$-$Z^1$, wherein:
$L^3$ represents —C(O)—;
$L^4$ represents $C_{1-6}$ alkylene (e.g. $C_4$ alkyl, such a n-butylene) optionally substituted with one or more fluoro; and
Z represents heterocyclyl (particularly wherein the heterocyclyl acts as a detectable group).

In alternative embodiments of the first aspect of the invention, the detectable label (or detectable group) may be a radioisotope. In such instances, the skilled person will understand that such radiolabelled compounds may be provided by replacement of one or more (e.g. one) of the atoms forming such compounds with a radioactive isotope thereof (such as by replacement of one or more H with the isotope tritium (T)), which may refer to enrichment of a sample of the compound so that a significant amount (e.g. at least 1%, at least 2%, at least 5% or at least 10% by weight, such as at least 20%, at least 30%, at least 40% or at least 50%, e.g. at least 90%) thereof has the relevant atom replaced with the radioisotope thereof.

Particular compounds of the invention that may be mentioned include those compounds as described in the examples provided herein, and pharmaceutically acceptable salts thereof. For the avoidance of doubt, where such compounds of the invention include compounds in a particular salt form, compounds of the invention include those compounds in non-salt form and in the form of any pharmaceutically acceptable salt thereof (which may include the salt form present in such examples).

Thus, particular compounds of the invention that may be mentioned include:

3-((9-amino-7-ethoxyacridin-3-yl)diazenyl)pyridine-2,6-diamine;
2-((9-amino-7-ethoxyacridin-3-yl)diazenyl)-3,6-dimethylphenol;
4-((9-amino-7-ethoxyacridin-3-yl)diazenyl)-3,5-dimethylphenol;
5-amino-2-((9-amino-7-ethoxyacridin-3-yl)diazenyl)phenol;
3-amino-2-((9-amino-7-ethoxyacridin-3-yl)diazenyl)phenol; and
4-((9-amino-7-ethoxyacridin-3-yl)diazenyl)-2,6-dimethylphenol, and pharmaceutically acceptable salts and/or detectably-labelled derivatives thereof.

More particular compounds of the invention that may be mentioned include:

2-((9-amino-7-ethoxyacridin-3-yl)diazenyl)-3,6-dimethylphenol;
4-((9-amino-7-ethoxyacridin-3-yl)diazenyl)-3,5-dimethylphenol;
5-amino-2-((9-amino-7-ethoxyacridin-3-yl)diazenyl)phenol;
3-amino-2-((9-amino-7-ethoxyacridin-3-yl)diazenyl)phenol; and
4-((9-amino-7-ethoxyacridin-3-yl)diazenyl)-2,6-dimethylphenol, and pharmaceutically acceptable salts and/or detectably-labelled derivatives thereof.

Medical Uses

As indicated herein, the compounds of the invention, and therefore compositions and kits comprising the same, are useful as pharmaceuticals.

Thus, according to a second aspect of the invention there is provided a compound of the invention, as hereinbefore defined (i.e. a compound as defined in the first aspect of the invention, including all embodiments and particular features thereof), for use as a pharmaceutical (or for use in medicine).

For the avoidance of doubt, references to compounds of the invention (i.e. compounds as defined in the first aspect of the invention) will include references to compounds of formula I (including all embodiments thereof, such as compounds of formula Ia, Ia', Ib, Ib', Ic and Id) and pharmaceutically acceptable salts and detectably-labelled derivatives thereof.

In particular embodiments of the second aspect of the invention (including all alternatives thereof), there is a proviso that certain compounds are excluded, or that the compound of formula I is not selected from a list of certain compounds, as described in the first aspect of the invention.

In a more particular embodiment of the second aspect of the invention, there is the proviso that the following compounds are excluded:

3-((9-amino-6-ethoxyacridin-3-yl)diazenyl)pyridine-2,6-diamine;
3-((9-amino-7-ethoxyacridin-3-yl)diazenyl)pyridine-2,6-diamine;
4-amino-2-((9-amino-7-ethoxyacridin-3-yl)diazenyl)naphthalene-1-sulfonic acid;
4-((9-amino-7-ethoxyacridin-3-yl)diazenyl)-2,6-dimethylphenol; and
4-amino-N-(5-((9-amino-7-ethoxyacridin-3-yl)diazenyl)thiazol-2-yl)benzenesulfonamide, and optionally pharmaceutically acceptable salts thereof.

In more particular embodiments (i.e. more particular embodiments of the second aspect of the invention), the compound of formula I is not a compound selected from the list consisting of:

3-((9-amino-6-ethoxyacridin-3-yl)diazenyl)pyridine-2,6-diamine;
3-((9-amino-7-ethoxyacridin-3-yl)diazenyl)pyridine-2,6-diamine;
4-amino-2-((9-amino-7-ethoxyacridin-3-yl)diazenyl)naphthalene-1-sulfonic acid;
4-((9-amino-7-ethoxyacridin-3-yl)diazenyl)-2,6-dimethylphenol; and
4-amino-N-(5-((9-amino-7-ethoxyacridin-3-yl)diazenyl)thiazol-2-yl)benzenesulfonamide.

In an alternative particular embodiment of the first aspect of the invention, there is the proviso that the following compounds are excluded:

3-((9-amino-7-ethoxyacridin-3-yl)diazenyl)pyridine-2,6-diamine;
4-amino-2-((9-amino-7-ethoxyacridin-3-yl)diazenyl)naphthalene-1-sulfonic acid;
4-((9-amino-7-ethoxyacridin-3-yl)diazenyl)-2,6-dimethylphenol; and
4-amino-N-(5-((9-amino-7-ethoxyacridin-3-yl)diazenyl)thiazol-2-yl)benzenesulfonamide, and optionally pharmaceutically acceptable salts thereof.

In alternative more particular embodiments (i.e. more particular embodiments of the first aspect of the invention), the compound of formula I is not a compound selected from the list consisting of:

3-((9-amino-7-ethoxyacridin-3-yl)diazenyl)pyridine-2,6-diamine;

4-amino-2-((9-amino-7-ethoxyacridin-3-yl)diazenyl)naphthalene-1-sulfonic acid;

4-((9-amino-7-ethoxyacridin-3-yl)diazenyl)-2,6-dimethylphenol; and 4-amino-N-(5-((9-amino-7-ethoxyacridin-3-yl)diazenyl)thiazol-2-yl)benzenesulfonamide.

In particular embodiments of the second aspect of the invention, the compound is a compound of formula I (including all embodiments thereof, such as compounds of formula Ia, Ia', Ib, Ib', Ic and Id) or a pharmaceutically acceptable salt thereof.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the active compounds of the invention to which they are metabolised), may also be described as "prodrugs".

For the avoidance of doubt, compounds of the invention are therefore useful because they possess pharmacological activity, and/or are metabolised in the body following oral or parenteral administration to form compounds that possess pharmacological activity. Compounds may also be useful in medicine as diagnostic agents (particularly compounds comprising datable labels, as described herein).

As described herein, compounds of the invention may be particularly useful in treating cancers, particularly cancers characterised by increased activity of the MYC pathway.

Thus, in a third aspect of the invention, there is provided a compound of the invention, as hereinbefore defined, for use in the treatment of a cancer characterised by increased activity of the MYC pathway.

In an alternative third aspect of the invention, there is provided a method of treating a cancer characterised by increased activity of the MYC pathway comprising administering to a patient in need thereof a therapeutically effective amount of a compound of the invention, as hereinbefore defined.

In a further alternative third aspect of the invention, there is provided the use of a compound of the invention, as hereinbefore defined, for the manufacture of a medicament for the treatment of a cancer characterised by increased activity of the MYC pathway.

The skilled person will understand that references to increased activity of the MYC pathway may refer to any instances where cancers have, in a significant number of cells thereof (e.g. at least 10%, such as at least 30%, at least 50%, at least 70%, or at least 90%) biological activity indicative of increased MYC activity when compared to the MYC activity observed in corresponding non-cancerous cells.

In such instances, the term "increased" may refer to the presence of MYC activity where such activity would not normally occur in corresponding non-cancerous cells, or to an increase in the level of activity when compared to corresponding non-cancerous cells, such as an at least 10% increase (e.g. an at least 50% increase or, more typically, an at least 100% increase). Such increased MYC activity may be observed in samples of such cancerous cells, and thus measured in relation to the given sample as a whole.

The skilled person will be aware that increased MYC activity may for instance refer to an increase in the expression of the MYC gene. For the avoidance of doubt, references to the MYC gene may include references to the MYC, MYCN and MYCL oncogenes.

The skilled person will also be aware that such increased MYC activity may result from a range of oncogenic alterations, such as:

increased copy number of the MYC, MYCN or MYCL oncogenes (which may be referred to as "copy number gain" or "gene amplification");

elevated/deregulated expression of MYC, MYCN or MYCL mRNA/protein; and/or increased activity of MYC-family proteins.

For the avoidance of doubt, references to increased copy number (i.e. gene amplification) of MYC-family (MYC, MYCN, MYCL) genes refer to the presence of additional copies of the relevant MYC gene in the genome of the cancerous cells when compared the corresponding non-cancerous cell-type.

The skilled person will be aware that copy number can be measured in situ by using techniques such as FISH (fluorescence in situ hybridization), NGS (next generation sequencing), or array-based analysis of copy number variations. The results obtained can be compared to copy number in corresponding normal (i.e. non-cancerous) cells. (e.g. where the cancer is of blood cells, the copy number in non-cancerous blood cells, such as those obtained from the same patient).

References to increased MYC activity may also refer to elevated MYC-family mRNA levels (overexpression) or to "deregulated" expression (meaning that the gene is expressed in the wrong cell at the wrong time). Expression changes can be caused by gene amplification (increased gene copy number) or, for instance, by altered cell signaling. Determination of whether MYC is overexpressed and/or deregulated may be made by comparison to a control sample. This control sample could be of normal (non-cancerous) cells from the same tissue, of benign tumors from the same tissue and/or of malignant tumours of lower grade. Levels of MYC expression be measured by RNA sequencing, RT-QPCR, microarray analysis, or by in situ hybridization.

As described herein, references to increased MYC activity may also refer to elevated and/or deregulated MYC-family protein levels. The skilled person will understand that such protein levels can be measured by, for instance, immunohistochemistry, western blot, RPPA (Reverse Phase Protein Array) and/or mass spectrometry. The skilled person will also understand that some tumours with low MYC mRNA might still have high protein levels due to for instance protein stabilization or increased MYC mRNA translation.

The skilled person will also understand that increased MYC activity may arise due to post-translational modifications and/or altered protein interactions in response to cell signalling, resulting in the activity rather than the level of the MYC proteins being increased. This results in activation (or repression) of MYC target genes, and can be measured using routine techniques, such as expression profiling of mRNA and/or protein by RT-QPCR, microarray analysis, RNA sequencing, western blot, protein arrays, and/or mass spectrometry.

For the avoidance of doubt, the above-mentioned factors resulting in increased MYC activity also be collectively referred to as "activation of the MYC pathway" or the like.

The skilled person will understand that references to the treatment of a particular condition (or, similarly, to treating that condition) will take their normal meanings in the field of medicine. In particular, the terms may refer to achieving a reduction in the severity and/or frequency of occurrence of one or more clinical symptom associated with the condition, as adjudged by a physician attending a patient having or being susceptible to such symptoms.

For example, in the case of the treatment of a cancer, the term may refer to achieving a reduction (e.g. at least a 5% reduction, such as at least a 10% or 20% reduction) in the number of cancer cells present and/or the volume of tumor mass (in the case of a solid tumor).

As used herein, references to a patient (or to patients) will refer to a living subject being treated, including mammalian (e.g. human) patients. In particular, references to a patient will refer to human patients.

For the avoidance of doubt, the skilled person will understand that such treatment will be performed in a patient (or subject) in need thereof. The need of a patient (or subject) for such treatment may be assessed by those skilled the art using routine techniques.

As used herein, the terms disease and disorder (and, similarly, the terms condition, illness, medical problem, and the like) may be used interchangeably.

As used herein, the term effective amount will refer to an amount of a compound that confers a therapeutic effect on the treated patient. The effect may be observed in a manner that is objective (i.e. measurable by some test or marker) or subjective (i.e. the subject gives an indication of and/or feels an effect). In particular, the effect may be observed (e.g. measured) in a manner that is objective, using appropriate tests as known to those skilled in the art.

Compounds of the invention may find particular utility in the treatment of cancers known to be frequently characterised by MYC amplification. Thus, in certain embodiments, the cancer is a cancer (or a combination of one or more cancers) selected from the list consisting of:
Burkitt's lymphoma;
ovarian cancer, such as ovarian cancer with BRCA alterations;
basal-like/triple negative breast cancer;
esophageal squamous cell carcinoma;
colon cancer;
endometrial cancer;
neuroblastoma;
small cell lung carcinoma;
medulloblastoma, in particular group 3;
pancreatic cancer;
head and neck cancer;
prostate cancer; and
hepatocellular carcinomas.

Pharmaceutical Compositions

As described herein, compounds of the invention are useful as pharmaceuticals. Such compounds may be administered alone or may be administered by way of known pharmaceutical compositions/formulations.

In a fourth aspect of the invention, there is provided a pharmaceutical composition comprising a compound of the invention as defined herein, and optionally one or more pharmaceutically-acceptable excipient.

In particular embodiments of the fourth aspect of the invention, there is a proviso that certain compounds are excluded, or that the compound of formula I is not selected from a list of certain compounds, as described in the first or second (e.g. the second) aspect of the invention.

As used herein, the term pharmaceutically-acceptable excipients includes references to vehicles, adjuvants, carriers, diluents, pH adjusting and buffering agents, tonicity adjusting agents, stabilizers, wetting agents and the like. In particular, such excipients may include adjuvants, diluents or carriers.

For the avoidance of doubt, references herein to compounds of invention being for particular uses (and, similarly, to uses and methods of use relating to compounds of the invention) may also apply to pharmaceutical compositions comprising compounds of the invention, as described herein.

Thus, in a fifth aspect of the invention, there is provided a pharmaceutical composition as defined in the fourth aspect of the invention (inlcuding all emboidments thereof) for use in the treatment of a cancer characterised by amplification of MYC (as defined herein, with reference to the third aspect of the invention and all embodiments thereof).

The skilled person will understand that compounds of the invention may act systemically and/or locally (i.e. at a particular site), and may therefore be administered accordingly using suitable techniques known to those skilled in the art.

The skilled person will understand that compounds and compositions as described herein will normally be administered orally, intravenously, subcutaneously, intratumorally, buccally, rectally, dermally, nasally, tracheally, bronchially, sublingually, intranasally, topically, by any other parenteral route or via inhalation, in a pharmaceutically acceptable dosage form.

Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, raccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

Depending on e.g. potency and physical characteristics of the compound of the invention (i.e. active ingredient), pharmaceutical formulations that may be mentioned include those in which the active ingredient is present in an amount that is at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The skilled person will understand that compounds of the invention may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 μg/kg of body weight per day (μg/kg/day) to about 200 μg/kg/day, preferably about 0.01 to about 10 μg/kg/day, and more preferably about 0.1 to about 5.0 μg/kg/day. For example, when administered orally, treatment with such compounds may comprise administration of a formulations typically containing between about 0.01 μg to about 2000 mg, for example between about 0.1 μg to about 500 mg, or between 1 μg to about 100 mg (e.g. about 20 μg to about 80 mg), of the active ingredient(s). When administered intravenously, the most preferred doses will range from about 0.001 to about 10 μg/kg/hour during constant rate infusion. In some instances, treatment may comprise administration of such compounds and compositions in a single daily dose, or the total daily dosage may be administered in divided doses of two, three or four times daily (e.g. twice daily with reference to the doses described herein, such as a dose of 25 mg, 50 mg, 100 mg or 200 mg twice daily).

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

For the avoidance of doubt, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. Although the above-mentioned dosages are exemplary of the average case, there can, of course, be individual instances where higher or lower dosage ranges are merited, and such doses are within the scope of the invention.

Combinations and Kits-of-Parts

The skilled person will understand that treatment with compounds of the invention may further comprise (i.e. be combined with) further treatment(s) for the same condition. In particular, treatment with compounds of the invention may be combined with means for the treatment of cancers (such as a type of cancer as described herein, e.g. cancers characterised by amplification of MYC), such as treatment with one or more other therapeutic agent that is useful in the in the treatment of such cancers and/or one or more physical method used in the treatment of such cancers (such as treatment through surgery), as known to those skilled in the art.

As described herein, compounds of the invention may also be combined with one or more other (i.e. different) therapeutic agents (i.e. agents that are not compounds of the invention) that are useful in the treatment of cancers, such as those cancers described herein. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a sixth aspect of the invention, there is provided a combination product comprising:

(I) a compound of the invention, as hereinbefore defined (i.e. in the first aspect of the invention, including all embodiments and particular features thereof); and (II) one or more other therapeutic agent that is useful in the treatment of cancer (such as a cancer as described herein), wherein each of components (I) and (II) is formulated in admixture, optionally with one or more a pharmaceutically-acceptable excipient.

In a seventh aspect of the invention, there is provided a kit-of-parts comprising:
(a) a pharmaceutical formulation as hereinbefore defined (i.e. in the fifth aspect of the invention); and
(b) one or more other therapeutic agent that is useful in the treatment of cancer (such as a cancer as described herein), optionally in admixture with one or more pharmaceutically-acceptable excipient,
which components (a) and (b) are each provided in a form that is suitable for administration in conjunction (i.e. concomitantly or sequentially) with the other.

In particular embodiments of the sixth and seventh aspects of the invention, there is a proviso that certain compounds are excluded, or that the compound of formula I is not selected from a list of certain compounds, as described in the first or second (e.g. the second) aspect of the invention.

In a more particular embodiment of the sixth and seventh aspects of the invention, there is the proviso that the following compounds are excluded:
3-((9-amino-6-ethoxyacridin-3-yl)diazenyl)pyridine-2,6-diamine; and
3-((9-amino-7-ethoxyacridin-3-yl)diazenyl)pyridine-2,6-diamine,
and optionally pharmaceutically acceptable salts thereof.

In more particular embodiments (i.e. more particular embodiments of the sixth and seventh aspects of the invention), the compound of formula I is not a compound selected from the list consisting of:
3-((9-amino-6-ethoxyacridin-3-yl)diazenyl)pyridine-2,6-diamine;
3-((9-amino-7-ethoxyacridin-3-yl)diazenyl)pyridine-2,6-diamine.

In an alternative embodiment, there is the proviso that the following compounds are excluded:
3-((9-amino-7-ethoxyacridin-3-yl)diazenyl)pyridine-2,6-diamine,
and optionally pharmaceutically acceptable salts thereof.

In further alternative embodiments, the compound of formula I is not a compound selected from the list consisting of:
3-((9-amino-7-ethoxyacridin-3-yl)diazenyl)pyridine-2,6-diamine.

With respect to the kits-of-parts as described herein, by "administration in conjunction with" (and similarly "administered in conjunction with") we include that respective formulations are administered, sequentially, separately or simultaneously, as part of a medical intervention directed towards treatment of the relevant condition.

Thus, in relation to the present invention, the term "administration in conjunction with" (and similarly "administered in conjunction with") includes that the two active ingredients (i.e. a compound of the invention and a further agent for the treatment of cancer, or compositions comprising the same) are administered (optionally repeatedly) either together, or sufficiently closely in time, to enable a beneficial effect for the patient, that is greater, over the course of the treatment of the relevant condition, than if either agent is administered (optionally repeatedly) alone, in the absence of the other component, over the same course of treatment. Determination of whether a combination provides a greater beneficial effect in respect of, and over the course of, treatment of a particular condition will depend upon the condition to be treated, but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of cancer, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

Other therapeutic agents useful in the treatment of cancers (such as those cancers as described herein) will be well-known to those skilled in the art. For example, such other therapeutic agents may include therapeutic agents routinely used in the treatment of the relevant cancer type, as will be known to those skilled in the art.

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable excipient.

In further aspects of the invention, there is provided a process for the preparation of a combination product or kit-of-parts as hereinbefore defined, which process comprises bringing into association a compound of the invention, as hereinbefore defined, with the other therapeutic agent that is useful in the treatment of the relevant disease or disorder, and at least one pharmaceutically-acceptable excipient.

As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention as described herein may be prepared in accordance with techniques that are well known to those skilled in the art, such as those described in the examples provided hereinafter.

According to an eighth aspect of the invention there is provided a process for the preparation of a compound of the invention as hereinbefore defined, comprising the step of:

reacting a compound of formula II

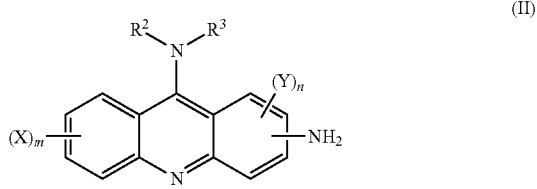

(II)

wherein $R^2$, $R^3$, X, Y, n and m are as defined herein (i.e. in the first aspect of the invention for compounds of formula I, including all embodiments thereof) with suitable source of nitrite (such as a metal nitrite salt, e.g. $NaNO_2$) in the presence of a suitable solvent (such as water) and a suitable acid (such as a suitable inorganic acid, e.g. $H_2SO_4$), followed by (i.e. followed immediately by, without isolation of intermediates) reaction with a compound of formula III

(III)

wherein $R^1$ is as defined herein (i.e. in the first aspect of the invention for compounds of formula I, including all embodiments thereof) in the presence of a suitable solvent (such as water) and a suitable base (such as a suitable metal carbonate, e.g. $Na_2CO_3$).

Compounds of formulae II and III are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, $3^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999), the contents of which are incorporated herein by reference.

Without wishing to be bound by theory, it is believed that compounds of the invention are able to treat cancers, particularly those cancers characterised by increased MYC activity, such as may be due to gene copy number alterations and/or increased expression/activity of MYC (i.e. activation of the MYC pathway), based on their ability to act as potent and specific inhibitors of MYC:MAX interaction, thus inhibiting MYC-dependent tumor cell growth.

It is also believed that detectably-labelled derivatives of compounds of the invention may be useful as diagnostic agents and/or as research tools, such as in drug development.

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

BRIEF DESCRIPTION OF THE FIGURES

FIG. 1: A) Microscale thermophoresis (MST) of fluorescently labeled MAX in a MYC:MAX heterodimer formation assay based on recombinant proteins. MST of labeled MAXbHLHZip after titration of Example 1 pre-incubated with 1 µM MYCbHLHZip, or with 1 µM MAXbHLHZip. Fluorescence intensity of labeled MAXbHLHZip relative DMSO was plotted against Example 1 concentration. B) Surface plasmon resonance (SPR) of MYC:MAX heterodimer formation assay. MAXbHLHZip was immobilized by an amino coupling procedure to a CM5 sensor chip. MYCbHLHZip pre-incubated with or without compound (as indicated) was injected over MAX for 180 seconds, allowed to dissociate for 240 seconds and regenerated. Reference surface (without MAXbHLHZip) subtracted sensorgrams are shown from one representative experiment. C) MYC binding response units (RU) plotted against Example 1 concentration from which an IC50 of Example 1 inhibition of MYC:MAX heterodimer formation is determined, summary of four experiments.

FIG. 2: A) MST assay of Example 1 effect on MYC and MAX, respectively. Recombinant MYC bHLHZip and MAX bHLHZip proteins were titrated, respectively, in a fixed concentration (3 µM) of Example 1. Changes in fluorescence were measured and normalized to control (buffer). Data are shown as mean±standard deviation of 6-8 biological repeats. B) MST assay of MYC (reverse MST). A fixed concentration of 200 nM labeled MYC was mixed with different concentrations of Example 1 as indicated. Data are shown as mean±standard deviation of 5 biological repeats. C) MST assay of Example 2 effect on MYC. D) MST assay of MYC with a control compound (non-binder).

FIG. 3: A) SPR assay to determine affinity of Example 1 to MYC. MYC bHLHZip protein was immobilized by aminocoupling on a CM5 sensor chip. Example 1 was injected at various concentrations in a kinetic experiment. The reference surface was subtracted from the analyte surface to generate a sensorgram. Association and dissociation rates ($k_a$=9294 M-1 s-1, $k_d$=0.02293 s-1) were determined using the Langmuir 1:1 model in the Biacore Evaluation program fitting curves with a constant Rmax of 43 RU (theoretical Rmax), thereby suggesting a $K_D$ of 2.5 µM with a $Chi^2$ value of 0.073. The sensorgram displays one representative experiment. Four kinetic experiments were carried out on two different sensor chips and an average $K_D$ of 1.6±0.5 µM was calculated. B) Four MYC equilibrium binding experiments with Example 1 summarized in an equilibrium binding plot. Binding affinities were estimated from the plot as 50% of Rmax suggesting a $K_D$ of approximately 1.5-2 mM with an experimental Rmax of 25-30 RU (theoretical Rmax=23 RU). Equilibrium binding experiments of MYC with Example 2 and control compound (non-binder) were plotted as well.

FIG. 4: A) Endogenous MYC:MAX (upper panel) and FRA1:JUN (lower panel) interactions as visualized as fluorescent red dots by isPLA. Nuclei were counterstained with DAPI (blue). Cells were treated with 10 µM of indicated compounds for 16 hours and subjected to isPLA using pairs of MYC and MAX and of FRA1 and JUN antibodies, respectively. As negative control, primary antibody pairs but only one oligo-conjugated secondary antibody was used. B) Quantification of MYC:MAX and C) FRA1:JUN isPLA, representing an average number of nuclear dots per cell from three microscopic fields normalized to corresponding values for DMSO-treated cells. D) Coimmunoprecipitation of endogenous MAX with MYC from MDA-MB231 cells treated with 5 µM Example 1 or DMSO for 3.5 hours. $1^{st}$-$4^{th}$ lanes from top; coimmunoprecipitated MAX, immunoprecipitated MYC, total levels of MAX and ACTIN, respectively, as determined by western blot analysis. E) MYC:MAX GLuc assay in cells. HEK293 cells transfected with MYC-GLuc-C and MAX-GLuc-N, and full length CMV-Luc. 24 hours later cells were treated with 10 mM of Example 1, Example 2 and control compound for 16 hours and thereafter analyzed in a dual luciferase assay. The ratio of *Gaussia*/Firefly luciferase luminescence were calculated and normalized to DMSO-treated cells.

FIG. 5: A) Inhibition of MYC transactivation of target genes (A) ODC1, (B) RSG16, and (C) CR2 as determined by RT-qPCR analysis, based on three biological experiments with three technical repeats each. U2OS-MYC-ER cells were treated with or without 100 nM 4-hydroxy-tamoxifen (HOT) for 4 hours, after which DMSO or Example 1 was added for 24 hours before total RNA was extraction. Fold changes in mRNA expression are presented relative to DMSO in non-HOT-treated cells after normalization to GAPDH, used as reference gene.

FIG. 6: A-B) Neuroblastoma cell lines with (SK-N-DZ, Kelly and IMR-32) or without (SK-N-F1, SK-N-RA and SK-N-AS) MYCN-amplification were exposed to different concentrations of Example 1, Example 2 and control compound, respectively, for 48 hours. Cell growth and viability was estimated by measuring metabolic activity. C) Growth of TGR-1 (wt), HO15.19 (MYC knockout) and HOmyc3 (MYC reconstituted HO15.19) Rat1 fibroblasts, as measured by the WST-1 assay after treatment with Example 1. Data are shown as mean±standard deviation of 3-5 biological experiments, each with 3 technical repeats.

FIG. 7: Example 1 inhibits MYC:MAX interaction, induces apoptosis and reduces tumor cell growth and microvascularity in a MYCN-amplified neuroblastoma mouse tumor model in vivo. SK-N-DZ MYCN-amplified neuroblastoma xenograft tumors reaching a volume of 100-200 $mm^3$ were treated with Example 1 (20 mg/kg body weight) or vehicle injected i.p. daily for 1-2 weeks. A) Apoptosis was determined by TUNEL staining of tumor tissues from mice treated with Example 1 or vehicle, counterstained with DAPI. Quantification of TUNEL staining was normalized to whole tumor areas as determined by DAPI from three Example 1- and three vehicle-treated mice. Student's t-test of Example 1 vs. vehicle; p=0.0083. B) Cell proliferation determined by Ki67 of tumor tissues from mice treated with Example 1 or vehicle, respectively, and counterstained with DAPI. Quantification of Ki67 negative areas normalized to whole tumor areas by DAPI from three Example 1- and three vehicle-treated mice. Student's t-test of Example 1 vs. vehicle; p=0.0380. C) Microvascular density visualized by CD31 staining in the red. C) Quantification of CD31 staining normalized to whole tumor areas from three Example 1- and three vehicle-treated mice. Student's t-test of Example 1 vs. vehicle; p=0.014. D) Detection of MYCN:MAX protein interaction by isPLA performed on tumor tissue from mice treated with Example 1 or vehicle using antibodies against MYCN and MAX. Quantification of MYCN:MAX isPLA signals in tumor tissue from Example 1- and vehicle-treated mice, presented as average number of dots from four randomly chosen microscopic fields from Example 1 treated mice normalized to corresponding values from vehicle-treated mice (F=28.102, P=0.008). E) Apoptosis determined from TUNEL stained tumor section derived from a MDA-MB231 xenograft mouse treated with Example 2 for 2 weeks. Quantification of apoptotic cells per counted field.

EXAMPLES

The present invention will be further described by reference to the following examples, which are not intended to limit the scope of the invention.

In the event that there is a discrepancy between nomenclature and any compounds depicted graphically, then it is the latter that presides (unless contradicted by any experimental details that may be given or unless it is clear from the context).

Experimental Procedures

Starting materials and intermediates used in the synthesis of compounds described herein are commercially available or can be prepared by the methods described herein or by methods known in the art.

Experiments were generally carried out under inert atmosphere (nitrogen or argon), particularly in cases where oxygen- or moisture-sensitive reagents or intermediates were used.

Mass spectrometry data are reported from liquid chromatography-mass spectrometry (LC-MS) using electrospray ionization. Chemical shifts for NMR data are expressed in parts per million (ppm, δ) referenced to residual peaks from the deuterated solvent used.

For syntheses referencing general procedures, reaction conditions (such as length of reaction or temperature) may vary. In general, reactions were followed by thin layer chromatography or LC-MS, and subjected to work-up when appropriate. Purifications may vary between experiments: in general, solvents and the solvent ratios used for eluents/ gradients were chosen to provide an appropriate $R_f$ and/or retention time.

For the preparation of Example 7 onwards, the following will apply (although such techniques may also apply to Examples 1 to 6).

1H NMR spectra were recorded using a Bruker DPX400 spectrometer (400 MHz) using deuterated solvents.

All evaporations were carried out in vacuum with a rotary evaporator at 10-30 mmHg. Analytical samples were dried under high vacuum (1-5 mmHg) at room temperature. Thin layer chromatography (TLC) was performed on silica gel plates (Merck) with fluorescent indicator. Spots were visualized by UV light (214 and 254 nm).

Flash chromatography was performed using silica gel 60 from Merck. All compounds evaluated in biological tests were purified to >95% as determined by HPLC-MS on an Agilent/HP 1200 system 6110 mass spectrometer with electrospray ionization (ESI+). HPLC-MS methods were the following. Method 1: Waters XBridge C18 3.5 μm column (3.0 mm×50 mm), 3.5 min gradient mobile phase [CH3CN]/ [10 mM NH4HCO3/H2O]. Method 2: ACE C18 3.5 μm column (3.0 mm×50 mm), mobile phase [0.1% TFA/ CH3CN]/[0.1% TFA/H2O]. Absorbance was monitored at 305±90 and 254 nm. All solvents used were HPLC grade. Preparative HPLC was performed on a Gilson HPLC system. Acidic pH: column ACE 5 C8 (150 mm×30 mm), H2O (containing 0.1% TFA), and MeCN were used as mobile phases at a flow rate of 45 mL/min, with a gradient time of 9 min.

Intermediate Compounds

Intermediate 1: 5-[(E)-(9-amino-7-ethoxy-acridin-3-yl)azo]-2-hydroxy-benzaldehyde $NaNO_2$ (28 mg, 0.42 mmol) in $H_2O$ (150 mL) was added to a stirred mixture of 6,9-diamino-2-ethoxyacridine lactate hydrate (150 mg, 0.41 mmol) and $H_2O$ (3 mL) at 0-5° C., immediately followed by the addition of $H_2SO_4$ (aq, 5%, 3 mL). The mixture was stirred at this temperature for 20 min and poured into a vigorously stirred 0-5° C. solution of 2-hydroxybenzaldehyde (56 mg, 0.46 mmol) and $Na_2CO_3$ (0.40 g, 3.8 mmol) in $H_2O$ (6 mL). The mixture was stirred at rt for 2 h and then pH was adjusted to ca 1 with HCl (aq, 2M) and then filtered. The dark solid was triturated in methanol (ca 10 mL) over the weekend and filtered and dried in vacuum to give the title compound, yield 120 mg (75%).

$H^1$ NMR (400 MHz, DMSO-$d_6$): δ ppm 1.44 (t, J=6.95 Hz, 3H) 4.21 (q, J=7.06 Hz, 2H) 7.21 (d, J=9.00 Hz, 1H) 7.70 (dd, J=9.16, 2.37 Hz, 1H) 7.88 (d, J=9.16 Hz, 1H) 7.94 (dd, J=9.32, 1.42 Hz, 1H) 7.98 (d, J=2.37 Hz, 1H) 8.15 (dd, J=8.92, 2.61 Hz, 1H) 8.22 (d, J=1.58 Hz, 1H) 8.24 (d, J=2.69 Hz, 1H) 8.74 (d, J=9.32 Hz, 1H) 9.77 (br. s., 2H) 10.38 (s, 1H)

Example Compounds

Example 1: 3-((9-amino-7-ethoxyacridin-3-yl)diazenyl)pyridine-2,6-diamine sulphate hydrate

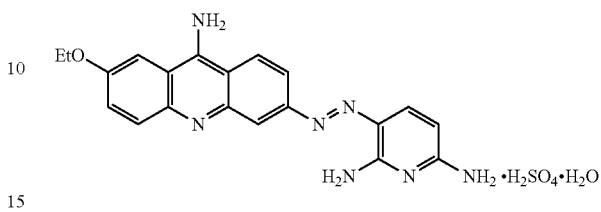

$NaNO_2$ (2.85 g, 41.31 mmol) in $H_2O$ (150 mL) was added to a stirred mixture of 6,9-diamino-2-ethoxyacridine lactate hydrate (15.00 g, 41.52 mmol) and $H_2O$ (300 mL) at 5° C., immediately followed by addition of $H_2SO_4$ (aq, 5%, 300 mL) at 5° C. The mixture was stirred at 5° C. for 20 min and poured into a vigorously stirred solution of 2,6-diaminopyridine (4.52 g, 4.14 mmol), $Na_2CO_3$ (40.0 g, 377 mmol) and $H_2O$ (600 mL). The mixture was stirred at rt for 12 h and filtered. The solids were collected, suspended in $H_2O$ (500 mL) and stirred at 60° C. for 6 h. The solids were collected, washed with $H_2O$ and dried in vacuo over $P_2O_5$ to give the title compound (15.50 g, 31.66 mmol, 76.3%).

$^1$H NMR (400 MHz, DMSO-$d_6$): 1.38 (t, J=7.0 Hz, 3H); 4.14 (q, J=7.0 Hz, 2H); 6.02 (d, J=8.8 Hz, 1H); 6.94 (br.s, 2H); 7.42 (dd, J=2.2, 9.2 Hz, 1H); 7.68 (d, J=8.8 Hz, 1H); 7.72 (d, J=2.2 Hz, 1H); 7.77 (d, J=9.2 Hz, 1H); 7.82 (dd, J=1.6, 9.2 Hz, 1H); 7.89 (d, J=1.6 Hz, 1H); 8.39 (d, J=9.2 Hz, 1H).

Following an analogous protocol, the compound of Example 1 was also prepared as the corresponding HCl salt. In the biological examples provided herein, these salts were used interchangeably.

Example 2: 4-((9-amino-7-ethoxyacridin-3-yl)diazenyl)-3,6-dimethylphenol

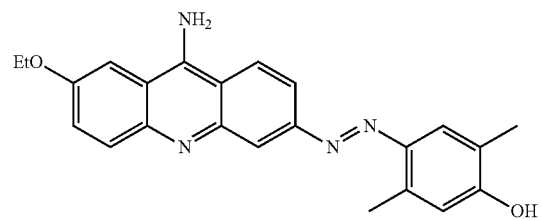 [SMILES: CCOc1ccc2nc3cc(/N=N/c4cc(C)c(O)cc4C)ccc3c(N)c2c1]

The title compound was prepared in accordance with Example 1.

$^1$H NMR (400 MHz, DMSO-$d_6$): δ 1.40 (t, J=7.0 Hz, 3H); 2.13 (s, 3H); 2.62 (s, 3H); 4.17 (q, J=7.0 Hz, 2H); 6.78 (s, 1H); 7.35 (dd, J=2.7, 9.4 Hz, 1H); 7.56 (s, 1H); 7.65 (d, J=2.6 Hz, 1H); 7.70 (dd, J=1.9, 9.4 Hz, 1H); 7.79 (d, J=9.4 Hz, 1H); 8.18 (d, J=1.9 Hz, 1H); 8.40 (d, J=9.4 Hz, 1H).

Example 3: 4-((9-amino-7-ethoxyacridin-3-yl)diazenyl)-3,5-dimethylphenol hydrate

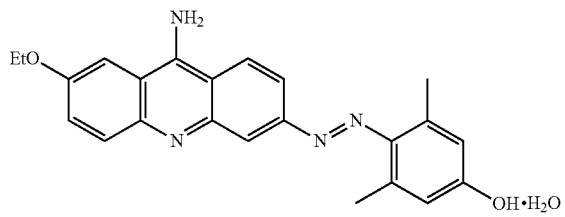

The title compound was prepared in accordance with Example 1.

$^1$H NMR (400 MHz, DMSO-d$_6$): δ 1.40 (t, J=7.0 Hz, 3H); 2.25 (s, 6H); 4.17 (q, J=7.0 Hz, 2H); 7.36 (dd, J=2.4, 9.2 Hz, 1H); 7.60 (s, 2H); 7.66 (d, J=2.4, 1H); 7.70 (dd, J=1.7, 9.4 Hz, 1H); 7.79 (d, J=9.4 Hz, 1H); 8.18 (d, J=1.7, 1H); 8.40 (d, J=9.4 Hz, 1H).

Example 4: 5-amino-2-((9-amino-7-ethoxyacridin-3-yl)diazenyl)phenol sulphate hydrate and

Example 5: 3-amino-2-((9-amino-7-ethoxyacridin-3-yl)diazenyl)phenol sulphate hydrate

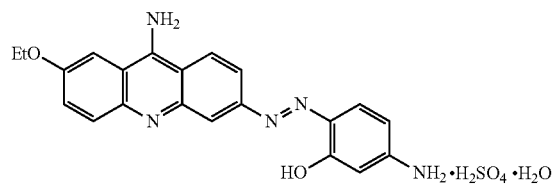

+

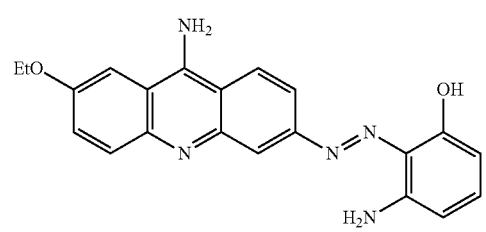

The mixture of the title compounds was prepared in accordance with Example 1.

$^1$H NMR (400 MHz, DMSO-d$_6$): δ 1.38 (t, J=7.0 Hz, 3H); 2.45 (s, 6H); 4.14 (q, J=7.0 Hz, 2H); 6.78 (s, 1H); 7.34 (d, J=9.2 Hz, 1H); 7.57 (s, 2H); 7.64 (unresolved d, 1H); 7.67 (d, J=9.6 Hz, 1H); 7.82 (d, J=9.6 Hz, 1H); 8.17 (d, J=1.9 Hz, 1H); 8.40 (d, J=9.2 Hz, 1H).

Example 6: 4-((9-amino-7-ethoxyacridin-3-yl)diazenyl)-2,6-dimethylphenol

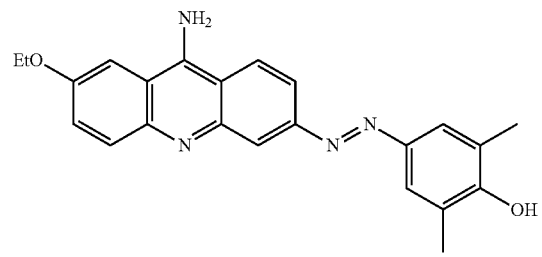 [SMILES: CCOc1ccc2nc3cc(/N=N/c4cc(C)c(O)c(C)c4)ccc3c(N)c2c1]

The title compound was prepared in accordance with Example 1.

$^1$H NMR (400 MHz, DMSO-d$_6$): δ 1.40 (t, J=7.0 Hz, 3H), 2.25 (s, 6H), 4.17 (q, J=7.0 Hz, 2H), 7.36 (dd, J=2.4, 9.2 Hz, 1H), 7.66 (s, 2H), 7.70 (dd, J=1.7, 9.4 Hz, 1H), 7.79 (d, J=9.4 Hz, 1H), 8.18 (d, J=1.7 Hz, 1H), 8.40 (d, J=9.4 Hz, 1H).

Example 7: 5-[(3aS,4S,6aR)-2-oxo-1,3,3a,4,6,6a-hexahydrothieno[3,4-d]imidazol-4-yl]-N-[[5-[(E)-(9-amino-7-ethoxy-acridin-3-yl)azo]-2-hydroxy-phenyl]methyl]-N-[2-(dimethylamino)ethyl]pentanamide

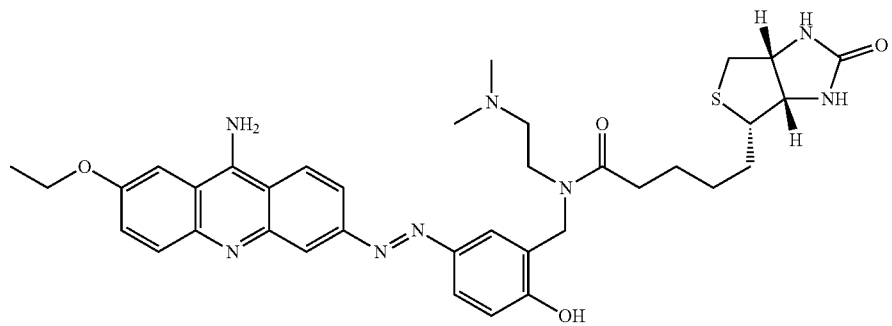 [SMILES: CCOc1ccc2nc3cc(/N=N/c4ccc(O)c(CN(CCN(C)C)C(=O)CCCC[C@@H]5SC[C@@H]6NC(=O)N[C@@H]65)c4)ccc3c(N)c2c1]

The title compound was prepared as follows. 4-[(E)-(9-amino-7-ethoxy-acridin-3-yl)azo]-2-[[2-(dimethylamino)ethylamino]methyl]phenol hydrochlorid (13 mg, 0.028 mmol) and (2,5-dioxopyrrolidin-1-yl) 5-[(3aS,4S,6aR)-2-oxo-1,3,3a4,6,6a-hexahydrothieno[3,4-d]imidazol-4-yl] pentanoate (10 mg, 0.029 mmol) was treated with triethylamine (10 µL, 0.072 mmol) in DMF (1 mL) at rt on. The reaction is clean and complete. The solution was diluted with some water and then purified by acidic preparative HPLC. The compound came rather early and it would have been a good idea to remove some DMF prior to the chromatography. The pure fractions were pooled and evaporated to give 5 mg of a yellow solid. the solid was treated with some MeOH and 2 M HCl, evaporated and dried in vacuum. The HCl salt was dissolved in a small amount of MeOH and diethyl ether was added. The formed solid was filtered off and dried in vacuum. Yield 3 mg.

Example 8: 4-[(E)-(9-amino-7-ethoxy-acridin-3-yl)azo]-2-[[2-(dimethylamino)ethylamino]methyl]phenol hydrochloride

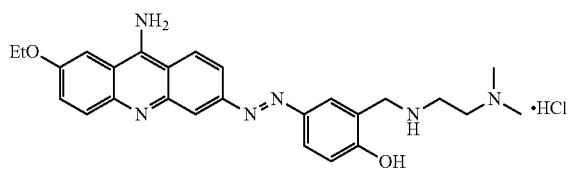 [SMILES: CCOc1ccc2nc3cc(/N=N/c4ccc(O)c(CNCCN(C)C)c4)ccc3c(N)c2c1 ; Cl]

Sodium cyanoborohydride (25 mg, 0.16 mmol) was added to a stirred solution of 5-[(E)-(9-amino-7-ethoxy-acridin-3-yl)azo]-2-hydroxy-benzaldehyde (25 mg, 0.065 mmol), N',N'-dimethylethane-1,2-diamine (15 µL, 0.14 mmol) in acetic acid (10%) in methanol (1 mL) and the reaction was left stirring at room temperature for 30 minutes. The reaction mixture was evaporated and re-dissolved in HCl (aq, 0.1M) and the solution was made basic with NaHCO$_3$ and the resulting solid was filtered of and washed with water. The crude material was purified by acidic reversed phase chromatography. The evaporated material was re-dissolved in methanol and acidified with HCl (aq, 0.1M) and evaporated to give the title compound, yield 8 mg (25%). The free base can be made by treating the hydrochloric salt with NaHCO$_3$, evaporating and re-dissolving in methanol.

$^1$H NMR (free base) (400 MHz, METHANOL-d$_4$) δ ppm 1.42 (t, J=6.95 Hz, 3H) 2.16 (s, 6H) 2.44 (t, J=7.27 Hz, 2H) 2.70 (t, J=7.19 Hz, 2H) 3.57 (d, J=1.90 Hz, 1H) 3.74 (s, 2H) 4.14 (q, J=6.90 Hz, 2H) 6.60 (d, J=8.53 Hz, 1H) 7.30 (dd, J=9.40, 2.61 Hz, 1H) 7.45 (d, J=2.21 Hz, 1H) 7.65 (dd, J=8.77, 2.13 Hz, 1H) 7.70-7.81 (m, 3H) 8.09 (s, 1H) 8.18 (d, J=9.32 Hz, 1H)

Example 9: 4-[(E)-(9-amino-7-ethoxy-acridin-3-yl)azo]-2-[[2-(dimethylamino)ethyl-methyl-amino]methyl]phenol

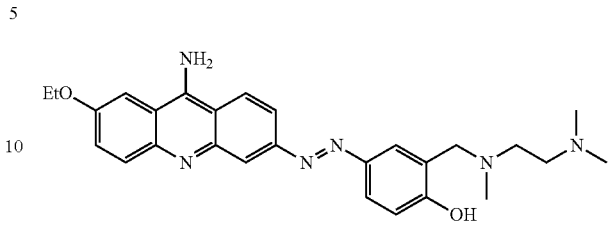

Sodium triacetoxyborohydride (60 mg, 0.28 mmol) was added to a stirred solution of 5-[(E)-(9-amino-7-ethoxy-acridin-3-yl)azo]-2-hydroxy-benzaldehyde (24 mg 0.06 mmol), N,N',N'-trimethylethane-1,2-diamine (15 µL, 0.12 mmol) and DIPEA (100 µL) in 1,2-dichloroethane (1.5 mL) and left stirring at room temperature overnight. The dark red solid was filtered off, re-dissolved in methanol and purified by acidic reversed phase chromatography to give the title product, yield 4 mg (14%).

$^1$H NMR (400 MHz, METHANOL-d$_4$) δ ppm 1.48 (t, J=6.95 Hz, 3H); 2.91 (s, 3H); 2.99 (s, 6H); 3.58-3.77 (m, 4H); 4.19 (q, J=6.95 Hz, 2H); 4.46 (s, 2H); 7.16 (d, J=8.69 Hz, 1H); 7.65 (dd, J=9.24, 2.61 Hz, 1H); 7.75 (d, J=2.37 Hz, 1H); 7.81 (d, J=9.32 Hz, 1H); 7.95 (dd, J=9.24, 1.82 Hz, 1H); 8.05 (dd, J=8.77, 2.45 Hz, 1H); 8.14 (dd, J=14.45, 1.97 Hz, 2H); 8.54 (d, J=9.16 Hz, 1H).

Example 10: 4-[(E)-2-(9-amino-7-ethoxyacridin-3-yl)diazen-1-yl]-2-(hydroxymethyl)phenol

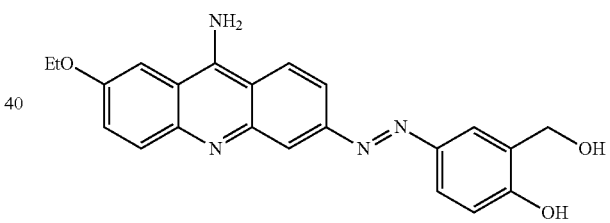

The title compound was prepared in accordance with the techniques described herein.

Example 11: 5-[(3aS,4S,6aR)-2-oxo-hexahydro-1H-thieno[3,4-d]imidazol-4-yl]-N-{2-[({5-[(E)-2-(9-amino-7-ethoxyacridin-3-yl)diazen-1-yl]-2-hydroxyphenyl}methyl)(methyl) amino]ethyl}-N-methylpentanamide

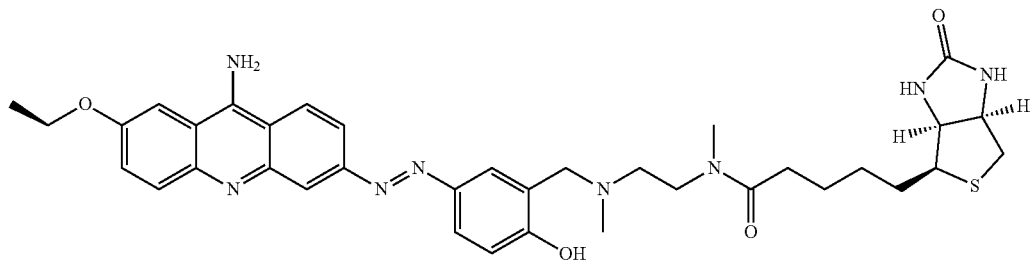

The title compound was prepared in accordance with the following general technique. Sodium triacetoxyborohydride (4 mg, 0.42 mmol) was added to a stirred solution of 5-[(E)-(9-amino-7-ethoxy-acridin-3-yl)azo]-2-hydroxy-benzaldehyde (0.005 mmol), N,N',N'-trimethylethane-1,2-diamine (0.01 mmol) and DIPEA (100 μL) in 1,2-dichloroethane (0.5 mL) and left stirring at room temperature for 1 h. Hplc showed that no sm is left and that the major product is the intended. Another portion of aldehyde, amine and hydride was added and the mixture diluted with more solvent (1 mL) and left stirring over the weekend. Where inefficient amination occurred two small lots were treated with a) more Sodium triacetoxyborohydride and b) diluted with MeOH and treated with NaCNBH3. Reaction (a) led to more reduction of the aldehyde whereas (b) gave more of the intended product. The main reaction was diluted with MeOH (2 mL) and treated with 3×40 mg of NaCNBH3 during 2 days. Purification was performed using silica gel chromatography (DCM/MeOH 4:1+0.1 Et3N).

Example 12: 4-[(E)-2-(9-amino-7-ethoxyacridin-3-yl)diazen-1-yl]-2-((dimethylamino) methyl)phenol

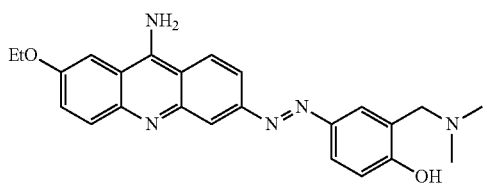 [SMILES: CCOc1ccc2nc3cc(/N=N/c4ccc(O)c(CN(C)C)c4)ccc3c(N)c2c1]

The title compound was prepared in accordance with the techniques described herein.
Biological Assays The biological activity of example compounds as described herein above was assessed using the following biological assays.

Biological Example 1: Inhibition of the MYC:MAX Interaction In Vitro as Analyzed by MST and SPR To analyze the effect of compounds on the MYC:MAX heterodimer formation, two biophysical assays were used; microscale thermophoresis (MST) and surface plasmon resonance (SPR).
Assay 1A. Microscale Thermophoresis (MST)

MST measures the movement of fluorescent labelled molecules in a microscopic temperature gradient. Changes in charge, size or of the hydration shell of the fluorescent molecule affects its migration in the temperature gradient, which can be detected by the fluorescence of the molecule (See Seidel et al., Microscale thermophoresis quantifies biomolecular interactions under previously challenging conditions, METHODS (2013)). Molecular interactions (such as protein-inhibitor interactions) affect the direction and speed of migration allowing quantification of the dissociation constant. MST was carried out on a Monolith NT.115 with blue/green filters according to manufacturer's protocol (NanoTemper). MYCbHLHZip and compounds were diluted and titrated in PBS supplemented with 0.05% Tween-20. Titration of protein was carried out in 16 PCR tubes into which a fixed concentration of fluorescent labelled protein was added. The mixture was applied to capillaries (standard treated, NanoTemper) and placed in the sample chamber of the Monolith NT.115. Capillaries were scanned to measure initial fluorescence of compound. MST was induced and fluorescence of the compound was measured during 40 seconds, indicative of thermophoresis. Double measurements were carried out (MST power of 20% and 40%, or 40% and 60%) for each sample. Relative fluorescence of labeled molecule normalized to control (only buffer) was plotted against titrated molecule concentration. In the MST MYC:MAX interaction assay 1 μM fluorescently labelled MAXbHLHZip was combined with a mixture of 1 μM MYCbHLHZip and different concentrations of example compound. Titration of Example 1 resulted in a thermophoresis shift of labelled MAX with a $K_d$ of 4.3+/−2.9 μM, indicating that the compound affected the MYC:MAX conformation, while having minor effects on labelled MAX when pre-mixed with 1 μM MAX instead of MYC (FIG. 1A), suggesting that Example 1 discriminates well between MYC:MAX and MAX:MAX interactions.
Assay 1B. Surface Plasmon Resonance (SPR)

The SPR method is a highly sensitive assay to determine the affinity between protein and ligand and to measure the kinetics of the interaction (see Handbook of Surface Plasmon Resonance 2nd edition, Richard B M Schasfoort (Editor), RSC 2017, ca. 500 p., hardcover, ISBN 978-1-78262-730-2). In the SPR assay, the target protein is immobilized on a dextran coated chip, and the ligand is injected over the immobilized protein. The Biacore T200 (GE Healthcare) measures adsorption of molecules on the chip by measuring the refractive index. When a ligand binds to the target protein, the refractive index, presented as response units (RU), is altered proportional to the change in mass on the chip, thereby allowing association and dissociation rates between the ligand and the target to be calculated. The SPR experiments were performed at 25° C. using a Biacore T200 (GE Healthcare) instrument. In the SPR MYC:MAX interaction assay MAXbHLHZip was covalently attached onto a CM5 sensor chip by amino coupling procedure resulting in immobilization levels of approximately 200-500 RU. 100 nM MYCbHLHZip pre-mixed with compound was injected over the MAXbHLHZip-surface and thereafter allowed to dissociate. Example 1 inhibited the MYC:MAX heterodimer formation with an IC50 of 3.8+/−1.2 μM (FIG. 1B-C). A summary of the results is provided in Table 1.

TABLE 1

Summary results for Biological Example 1

| Ex. | Assay 1A. MYC:MAX MST assay Kd (μM) | Assay 1B. MYC:MAX SPR assay IC50 (μM) |
|---|---|---|
| 1 | 4.3 +/− 2.9 | 3.8 +/− 1.2 |

Biological Example 2: Binding and Affinity to MYC Analyzed by MST and SPR

To analyze the direct binding of compounds to MYC, the effect on MYC in solution was analyzed by microscale thermophoresis (MST) and the direct binding and affinity to MYC was analyzed by surface plasmon resonance (SPR).
Assay 2A. MYC Binding MST Assay The MYC MST assay was performed as described above (Biological example 1—Assay 1A), except that the fluorescent molecule was either protein or Example 1. The example compound was kept at a fix concentration of 3 μM in PBS supplemented with 0.05% Tween-20, while MYCbHLHZip or MAX was titrated. The migration of example compound changed at MYC protein concentrations above 1 µM, but was unaffected with MAX up to highest concentration tested (15 µM) (FIG. 2A). In a reverse experiment, Example 1 was titrated in a fixed protein concentration in PBS supplemented with 0.05% Tween-20 and 1% DMSO as described above after labelling primary amines of the protein using the Protein labelling kit GREEN-NHS (NanoTemper) according to manufacturer's protocol. MYC protein concentration was estimated to be approximately 200 nM, not counting for protein loss during the labelling procedure. Migration of MYC was affected at compound concentrations above 200-400 nM (FIG. 2B). MST for Example 2 was carried out as in (A). Migration of Example 2 changed dramatically at 2 µM (and higher) of MYC (FIG. 2C). No effects on MYC thermophoresis was seen with a non-binding control compound (referred to as "6:1").

Assay 2B. MYC SPR Assay

To analyze the direct binding of compounds to MYC, the direct binding of compounds to MYC was detected by surface plasmon resonance (SPR) as described above (Biological example 1—Assay 1B). An amino coupling procedure was used to immobilize MYCbHLHZip protein on a CM5 sensor chip (GE Healthcare) resulting in immobilization levels of approximately 800 respectively 1000 RU. The compounds were injected at different concentrations, one at a time, over the surface for 50-80 seconds with a flow rate of 30 µl/min. Afterwards the compounds were allowed to dissociate for 240 seconds in running buffer (137 mM NaCl, 2.7 mM KCl, 10 mM $Na_2HPO4$, 1.8 mM $KH_2PO4$, 0.005% Tween-20, 1% DMSO, pH 7.4). To remove all remaining analyte the surface was regenerated with 2M Urea for 30 seconds and thereafter 1M NaCl, 2.7 mM KCl, 10 mM $Na_2HPO4$, 1.8 mM $KH_2PO4$, 1% DMSO, pH 7.4 for 30 seconds. Sensorgrams were generated by subtraction of the reference (blank immobilized) surface. Binding responses were related to respective compounds' Rmax. Rmax is the maximum response of a compound when it binds with a 1:1 stochiometry to the protein; Rmax=(MW analyte/MW ligand)×immobilized ligand level on the chip (RU) x stoichiometry (1:1). Kinetic experiments were carried out where recombinant MYC bHLHZip was immobilized on the chip and different concentrations of Example 1 were injected as above. Association and dissociation rates of the compound were obtained from a 1:1 Langmuir model after subtraction of reference cell values, suggesting a $K_D$ value of 1.6±0.5 µM (FIG. 3A). From equilibrium binding experiments, a $K_D$ value of approximately 1.5-2 µM was determined by an equilibrium binding plot (FIG. 3B). Example 2-6 were analyzed for their MYC binding properties by equilibrium binding experiments as described for example 1. A summary of the results is provided in Table 2.

TABLE 2

Summary of results from Biological Example 2

| Ex. | Assay 2A.<br>MYC:MAX MST assay.<br>Effect on<br>thermophoresis (µM) | Assay 2B.<br>MYC SPR Assay.<br>Binding relative to Rmax<br>(Response Units) |
|---|---|---|
| 1 | ≥1 | 1.6 |
| 2 | ≥2 | 1.2 |
| 3 | NT | 1.5 |
| 4-5 | NT | 0.6 |
| 6 | NT | 0.8 |

NT = not tested

Biological Example 3: MYC:MAX Interactions in Cells as Shown by CoIP, isPLA and GLuc Assays To analyze the MYC:MAX interaction in cells, three assays were used, in situ proximity ligation assay (isPLA), coimmunoprecipitation (CoIP), and *Gaussia* luciferase complementation assay (GLuc).

Assay 3A: The isPLA Assay

Identification of endogenous protein-protein interactions in fixed cells and has been described (Soderberg, O. et al., Nat Methods, 3, 995-1000 (2006)). MDA-MB231 cells were grown on collagen-coated chamber slides (Falcon), treated with 10 µM Example 1 for 24 hours, thereafter washed twice with PBS and fixed in ice cold methanol for 15 min at room temperature. Slides were washed in PBS with 0.05% Tween 20 and incubated in blocking buffer after which isPLA was performed using the Duolink® in situ PLA kit (Sigma-Aldrich) according to the manufacturer's protocol. DNA was stained with DAPI. Incubation with primary antibodies directed to MYC and MAX, or FRA-1 and JUN, respectively, were performed at +4° C. overnight. Endogenous MYC:MAX or FRA-1:JUN protein interactions were visualized by fluorescence microscopy as fluorescent dots mainly localized in the cell nucleus. Images were taken using an Axiovert 200M inverted microscope (Zeiss) and fluorescent dots were quantified using semi-automated analysis in ImageJ (http://imagej.net) and averaged to number of dots per cell. Example 1 significantly decreased isPLA signals to 7% of DMSO control, while not affecting the interaction between the bZip transcription factors FRA1 and JUN (FIG. 4A-C).

Assay 3B: CoIP

Coimmunoprecipitation of endogenous MYC:MAX proteins were essentially carried out as in Bahram, F. et al. Interferon-gamma-induced p27KIP1 binds to and targets MYC for proteasome-mediated degradation. Oncotarget 7, 2837-2854, doi:10.18632/oncotarget.6693 (2016). MDA-MB231 cells were treated with 5 µM Example 1 for 3.5 hours post-harvesting. Endogenous MAX was coimmuno-precipitated with MYC.

Example 1 Reduced the MYC:MAX Protein Interaction by More than Half of the DMSO Treated Cells (FIG. 4D)

Assay 3C: GLuc Assay

The protein fragment complementation assay using the *Gaussia* luciferase (GLuc) has been described (Remy, I. & Michnick, S. W. A highly sensitive protein-protein interaction assay based on *Gaussia* luciferase. Nat Methods 3, 977-979, doi:10.1038/nmeth979 (2006)). 0.2 µg of each GLuc-construct (MAX-GLuc-N+MYC-GLuc-C) together with 0.05 µg pCMV-Luc (Firefly luciferase) were used for transfection of HEK293 or COS-7 cells. 24 hours later cells were treated with compound or DMSO. After another 17 hours the cells were harvested and lyzed in passive lysis buffer (Promega) supplemented with complete protease inhibitor (Roche). After 60 min incubation at room temperature 20 µM D-luciferin was added (substrate of Firefly luciferase) and luminescence was measured in a Lumat LB9501 (Berthold) or OmegaFluostar (BMG Labtech) luminometer. Directly after, the *Gaussia* luciferase substrate Coelenterazine (Promega) was added to a final concentration of 20 µM and the luciferase activity was measured. The ratio between *Gaussia* and Firefly luciferase values were calculated and normalized to DMSO-treated control cells. Example 1 inhibited exogenous MYC:MAX protein interactions with an IC50 of 10 µM. Example 2 inhibited 65% of the MYC:MAX interactions at 10 µM (FIG. 4E).

TABLE 3

Summary of results from Biological Example 3

MYC:MAX interaction assays in cells

| Ex. | Assay 3A: isPLA assay (inhibition at 10 µM) | Assay 3B: CoIP (inhibition at 10 µM) | Assay 3C: GLuc assay (inhibition at 10 µM) |
|---|---|---|---|
| 1 | 95% | >70% | 50% |
| 2 | NT | NT | 65% |

Biological Example 4: MYC Target Gene Expression

Assay 4: Gene Expression

To investigate the effect of the compounds on MYC-driven transcription, we utilized U2OS cells containing a MYC-estrogen receptor (MYC-ER) fusion protein, the activity of which is regulated by the ligand 4-hydroxytamoxifen (HOT). RT-qPCR was performed essentially as described in Bahram, F. et al. Interferon-gamma-induced p27KIP1 binds to and targets MYC for proteasome-mediated degradation. Oncotarget 7, 2837-2854, doi:10.18632/oncotarget.6693 (2016). Activation of MYC (vehicle control+HOT) for 24 hours resulted in increased expression of three previously described direct MYC target genes, OC1, RSG16 and CR2. Treatment with Example 1 significantly reduced HOT-induced expression of all three genes (FIG. 5A-C) indicating that Example 1 inhibits MYC-driven transcription, which is expected of a potent MYC:MAX inhibitor.

TABLE 4

Summary of results from Biological Example 4

Assay 4. MYC:MAX inhibition of gene expression at 10 µM.

| Ex. | ODC1 gene | RSG16 gene | CR2 gene |
|---|---|---|---|
| 1 | 100% | 68% | 100% |

Biological Example 5: MYC-Dependent Cell Growth Inhibition as Measured by Metabolic Activity Assay (WST-1)

MYC-dependent cell growth inhibition was analyzed in neuroblastoma cell lines and immortal Rat1 fibroblasts (Tgr) cell lines with different MYC statuses.

Assay 5A: Neuroblastoma Cell Growth

Neuroblastoma cell lines with (SK-N-DZ, Kelly and IMR-32) or without (SK-N-F1, SK-N-RA and SK-N-AS) MYCN-amplification were exposed to different concentrations of example compounds for 48 hours. Cell growth and viability was estimated by measuring metabolic activity by incubating cells in triplicates with WST-1 (Roche) in medium at 37° C. and 5% $CO_2$ for 2 hours after which absorbance was measured with an Omega Fluostar (BMG Labtech) in a 96 well plate format. Example 1 reduced growth of the MYCN-amplified cell lines significantly stronger than of the MYCN-non-amplified cell lines with an average growth inhibition of 50% (GI50) value of 2.5-6 and >20 µM, respectively (FIG. 6A), thereby showing selectivity for MYC-driven tumors cells. Examples 2-6 and 8-9 also discriminated between cells dependent on MYCN status (FIG. 6B). Examples 10-12 have growth inhibition activities in MYCN-driven tumor cells.

Assay 5B: Tgr Cell Growth

Tgr cells were treated at 37° C. and 5% $CO_2$ at 48 hours with Example and Example 2. H015.19 is a MYC null rat cell line derived from Tgr1 (parental cells), while H0Myc3 cells were generated from the MYC null cells by reconstitution of a MYC gene(Mateyak, M. K., Obaya, A. J., Adachi, S. & Sedivy, J. M. Phenotypes of c-Myc-deficient rat fibroblasts isolated by targeted homologous recombination. Cell Growth Differ 8, 1039-1048 (1997)). Example 1 strongly inhibited growth of wt and reconstituted cells, but did not significantly affect growth of the MYC null cells, thus showing a clear difference in response between MYC expressing and MYC-deficient cells (FIG. 6C). Example 2 also discriminated between cells dependent on MYC status (FIG. 6C).

TABLE 6

Summary of results from Biological Example 5 (first run)

MYC-dependent cell growth inhibition

| | Neuroblastoma cells | | Immortal Rat1 fibroblast (Tgr) cells | |
|---|---|---|---|---|
| Ex. | MYCN-amplified cells (GI50 µM) | non-MYCN-amplified cells (GI50 µM) | Tgr and H0Myc3 cells (GI50 µM) | MYC null (H015.19) cells (GI50 µM) |
| 1 | 2.5-6 | >25 | 4 | >>10 |
| 2 | 4 | 12.5 | NT | NT |

TABLE 7

Summary of results from Biological Example 5 (second run)

MYC-dependent cell growth inhibition
Neuroblastoma cells

| Ex. | MYCN-amplified cells (GI50 µM) | non-MYCN-amplified cells (GI50 µM) |
|---|---|---|
| 1 | 2.5 | >25 |
| 2 | 2.5 | 10 |
| 3 | 2 | >25 |
| 4 and 5 | 20 | >25 |
| 6 | 1 | >25 |
| 7 | | |
| 8 | 4 | 10 |
| 9 | 6 | 11 |
| 10 | 15 | NT |
| 11 | | |
| 12 | 25 | NT |

Biological Example 6: Bioactivity in MYC-Dependent Mouse Tumor Models

To validate the efficacy of Example 1 in tumor tissue in vivo, we utilized a mouse xenograft tumor model based on human MYCN-amplified SK-N-DZ neuroblastoma cells. Tumor cells ($5 \times 10^6$) were injected into the flank of athymic nude mice and allowed to form tumors after which Example 1 or vehicle were administered by daily intraperitoneal injection at a dose of 20 mg/kg body weight for 1-2 weeks.

TUNEL-staining of tumor sections revealed a dramatic increase in apoptotic tumor areas (FIG. 7A) and a significant increase in non-proliferative areas as determined by Ki67 staining (FIG. 7B) in tumors from compound-treated mice compared with vehicle-treated mice. CD31 staining of endothelial cells revealed a significantly reduced microvascular density (MVD) in compound-treated mice compared with vehicle-treated mice (FIG. 7C). isPLA analysis showed a significant reduction in MYCN:MAX interactions in tumors from compound-treated compared to vehicle-treated mice (FIG. 7D), indicating that Example 1 reaches and is active against its target in vivo.

TABLE 7

Summary of results from Biological Example 6

Assay 7. In vivo mouse tumor model
Molecular characteristics

| Ex. | TUNEL Increase in apoptotic tumor area relative to vehicle (%) | Ki67 Increase in Ki67-negative tumor area relative to vehicle (%) | CD31 Decrease in microvascular density (% of vehicle) | MYCN:MAX isPLA Decrease in MYCN:MAX isPLA signal (% of vehicle) |
|---|---|---|---|---|
| 1 | 1420 | 550 | 44 | 66 |

The invention claimed is:
1. A method of treating a cancer characterised by increased MYC activity comprising administering to a patient in need thereof a therapeutically effective amount of a compound, or a pharmaceutically acceptable salt and/or detectably labelled derivative thereof, wherein the compound is represented by formula I:

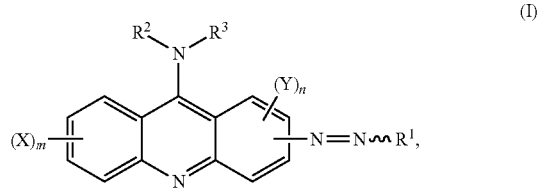

wherein:
R$^1$ represents aryl optionally substituted by one or more groups independently selected from G$^{1c}$, and heteroaryl optionally substituted by one or more groups independently selected from G$^{1d}$;
R$^2$ and R$^3$ each represent H;
m represents 0, 1, 2, 3 or 4;
n represents 0, 1, 2 or 3;
each X independently represents —OR$^{12}$ or H;
each Y independently represents halo, R$^{a3}$, —CN, -A$^{a2}$-C(O)R$^{b3}$, -A$^{b2}$-C(O)N(R$^{c3}$)R$^{d3}$, -A$^{c2}$-C(O)OR$^{e3}$, -A$^{d2}$-S(O)$_p$R$^{f3}$, -A$^{e2}$-S(O)$_p$N(R$^{g3}$)R$^{h3}$, -A$^{f2}$-S(O)$_p$OR$^{i3}$, —N(R$^{j3}$)R$^{k3}$, —OR$^{l3}$ or —SR$^{m3}$;
each A$^{a2}$, A$^{b2}$, A$^{c2}$, A$^{d2}$, A$^{e2}$, and A$^{f2}$ independently represents a single bond, —N(R$^{n3}$)— or —O—;
each G$^{1c}$ and G$^{1d}$ independently represents halo, R$^{a4}$, —CN, -A$^{a3}$-C(Q$^{a2}$)R$^{b4}$, -A$^{b3}$-C(Q$^{b2}$)N(R$^{c4}$)R$^{d4}$, -A$^{c3}$-C(Q$^{c2}$)OR$^{e4}$, -A$^{d3}$-S(O)$_p$R$^{f4}$, -A$^{e3}$-S(O)$_p$N(R$^{g4}$)R$^{h4}$, -A$^{f3}$-S(O)$_p$OR$^{i4}$, —N$_3$, —N(R$^{j4}$)R$^{k4}$, —N(H)CN, —NO$_2$, —ONO$_2$, —OR$^{l4}$, —SR$^{m4}$, —B(OR$^{n4}$)$_2$, —P(O)(N(R$^{o4}$)R$^{p4}$)$_2$, —P(O)(N(R$^{o4}$)R$^{p4}$)(OR$^{q4}$), —P(O)(OR$^{r4}$)$_2$, or =Q$^{d2}$;

each A$^{a3}$, A$^{b3}$, A$^{c3}$, A$^{d3}$, A$^{e3}$, and A$^{f3}$ independently represents a single bond, —C(O)N(R$^{s4}$)—, —N(R$^{t4}$)— or —O—;
each Q$^{a2}$, Q$^{b2}$, Q$^{c2}$, and Q$^{d2}$ independently represents =O, =S, =C(H)NO$_2$, =N(CN), =NR$^{u4}$, =NN(R$^{v4}$)R$^{w4}$, =N(OR$^{x4}$), or =NS(O)$_p$N(R$^{v4}$)R$^{w4}$;
each R$^{12}$ independently represents H, C$_{1-12}$ alkyl, C$_{2-12}$ alkenyl or C$_{2-12}$ alkynyl each optionally substituted by one or more groups independently selected from G$^{3a}$ and heterocyclyl optionally substituted by one or more groups independently selected from G$^{3b}$;
each R$^{a3}$ and R$^{f3}$ independently represents C$_{1-6}$ alkyl optionally substituted by one or more F;
each R$^{b3}$, R$^{c3}$, R$^{d3}$, R$^{e3}$, R$^{g3}$, R$^{h3}$, R$^{i3}$, R$^{j3}$, R$^{k3}$, R$^{l3}$, R$^{m3}$ and R$^{n3}$ independently represents H or C$_{1-6}$ alkyl optionally substituted by one or more F, or alternatively any of R$^{c3}$ and R$^{d3}$, R$^{g3}$ and R$^{h3}$ and/or R$^{j3}$ and R$^{k3}$, are linked together to form, together with the nitrogen atom to which they are attached, a 3- to 6-membered ring, which ring optionally contains one further heteroatom and which ring optionally is substituted by one or more groups independently selected from F, C$_{1-3}$ alkyl optionally substituted by one or more F, and =O;
each R$^{a4}$ and R$^{f4}$ independently represents C$_{1-8}$ alkyl, C$_{2-8}$ alkenyl or C$_{2-8}$ alkynyl each optionally substituted by one or more groups independently selected from G$^{4a}$, heterocyclyl optionally substituted by one or more groups independently selected from G$^{4b}$, aryl optionally substituted by one or more groups independently selected from G$^{4c}$, and heteroaryl optionally substituted by one or more groups independently selected from G$^{4d}$;
each R$^{b4}$, R$^{c4}$, R$^{d4}$, R$^{e4}$, R$^{g4}$, R$^{h4}$, R$^{i4}$, R$^{j4}$, R$^{k4}$, R$^{l4}$, R$^{m4}$, R$^{n4}$, R$^{o4}$, R$^{p4}$, R$^{q4}$, R$^{r4}$, R$^{s4}$, R$^{t4}$, R$^{u4}$, R$^{v4}$, R$^{w4}$ and R$^{x4}$ independently represents H or C$_{1-8}$ alkyl, C$_{2-8}$ alkenyl or C$_{2-8}$ alkynyl each optionally substituted by one or more groups independently selected from G$^{4a}$, heterocyclyl optionally substituted by one or more groups independently selected from G$^{4b}$, aryl optionally substituted by one or more groups independently selected from G$^{4c}$, and heteroaryl optionally substituted by one or more groups independently selected from G$^{4d}$, or alternatively any of R$^{c4}$ and R$^{d4}$, R$^{g4}$ and R$^{h4}$, R$^{j4}$ and R$^{k4}$, R$^{o4}$ and R$^{p4}$ and/or R$^{v4}$ and R$^{w4}$ are linked together to form, together with the nitrogen atom to which they are attached, a 3- to 6-membered ring, which ring optionally contains one further heteroatom and which ring optionally is substituted by one or more groups independently selected from halo, C$_{1-3}$ alkyl, C$_{2-3}$ alkenyl and C$_{2-3}$ alkynyl each optionally substituted by one or more halo, and =O, or alternatively
two R$^{n4}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halo, C$_{1-3}$alkyl optionally substituted by one or more halo, and =O, or alternatively
two R$^{r4}$ are linked together to form, along with the phosphorus, and the oxygen atoms to which they are attached, a 5- to 8-membered heterocyclic ring, which ring optionally contains one or more further heteroatoms and which ring optionally is substituted by one or more groups independently selected from halo, $C_{1-3}$ alkyl optionally substituted by one or more halo, and =O;

each $R^{v6}$ and $R^{x6}$ idenpendently represents H or $C_{1-6}$ alkyl optionally substituted by one or more F;

each $G^{3a}$ and $G^{3b}$ independently represents halo, $R^{a6}$, —CN, -$A^{a5}$-C($Q^{a4}$)$R^{b6}$, -$A^{b5}$-C($Q^{b4}$)N($R^{c6}$)$R^{d6}$, -$A^{c5}$-C($Q^{c4}$)O$R^{e6}$, -$A^{d5}$-S(O)$_p$$R^{f6}$, -$A^{e5}$-S(O)$_p$N($R^{g6}$)$R^{h6}$, -$A^{f5}$-S(O)$_p$O$R^{i6}$, —N$_3$, —N($R^{k6}$, -N(H)CN, -NO$_2$, -ONO$_2$, -O$R^{l6}$, -S$R^{m6}$-B(O$R^{n6}$)$_2$, -P(O)(N($R^{o6}$)$R^{p6}$)$_2$, -P(O)(N($R^{o6}$)$R^{p6}$)(O$R^{q6}$), -P(O)(O$R^{r6}$)$_2$, or =$Q^{d4}$;

each $A^{a5}$, $A^{b5}$, $A^{c5}$, $A^{d5}$, $A^{e5}$, and $A^{f5}$ independently represents a single bond, -C(O)N($R^{s6}$)-, -N($R^{t6}$)— or -O-;

each $Q^{a4}$, $Q^{b4}$, $Q^{c4}$, and $Q^{d4}$ independently represents =O, =S, =C(H)NO$_2$, =N(CN), =N$R^{u6}$, =NN($R^{v6}$)$R^{w6}$, =N(O$R^{x6}$), or =NS(O)$_p$N($R^{v6}$)$R^{w6}$;

each $R^{v6}$ and $R^{x6}$ independently represents H or $C_{1-6}$ alkyl optionally substituted by one or more F;

each $R^{a6}$ and $R^{f6}$ independently represents $C_{1-6}$ alkyl, $C_{2-6}$ alkenyl or $C_{2-6}$ alkynyl, each optionally substituted by one or more groups independently selected from $G^{5a}$, heterocyclyl optionally subtituted by one or more groups independently selected from $G^{5b}$, aryl optionally substituted by one or more groups independently selected from $G^{5c}$, and heteroaryl optionally substituted by one or more groups independently selected from $G^{5d}$;

each $R^{b6}$, $R^{c6}$, $R^{d6}$, $R^{e6}$, $R^{g6}$, $R^{h6}$, $R^{i6}$, $R^{j6}$, $R^{k6}$, $R^{l6}$, $R^{m6}$, $R^{n6}$, $R^{o6}$, $R^{p6}$, $R^{q6}$, $R^{r6}$, $R^{s6}$, $R^{t6}$, $R^{u6}$, $R^{v6}$, $R^{w6}$ and $R^{x6}$, independently represents H or independently represents $C_{1-6}$ alkyl, $C_{2-6}$ alkenyl or $C_{2-6}$ alkynyl, each optionally substituted by one or more groups independently selected from $G^{5a}$, heterocyclyl optionally substituted by one or more groups independently selected from $G^{5b}$, aryl optionally substituted by one or more groups independently selected from $G^{5c}$, and heteroaryl optionally substituted by one or more groups independently selected from $G^{5d}$, or alternatively any of $R^{c6}$ and $R^{d6}$, $R^{g6}$ and $R^{h6}$, $R^{j6}$ and $R^{k6}$, $R^{o6}$ and $R^{p6}$ and/or $R^{v6}$ and $R^{w6}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $G^{4a}$, $G^{4b}$, $G^{4c}$ and $G^{4d}$ independently represents halo, $R^{a7}$, —CN, -$A^{a6}$-C($Q^{a5}$)$R^{b7}$, -$A^{b6}$-C($Q^{b5}$)N($R^{c7}$)$R^{d7}$, -$A^{c6}$-C($Q^{c5}$)O$R^{e7}$, -$A^{d6}$-S(O)$_p$$R^{f7}$, -$A^{e6}$-S(O)$_p$N($R^{g7}$)$R^{h7}$, -$A^{f6}$-S(O)$_p$O$R^{i7}$, —N$_3$, —N($R^{j7}$)$R^{k7}$, —N(H)CN, —NO$_2$, —ONO$_2$, —O$R^{l7}$, —S$R^{m7}$—B(O$R^{n7}$)$_2$, —P(O)(N($R^{o7}$)$R^{p7}$)$_2$, —P(O)(N($R^{o7}$)$R^{p7}$)(O$R^{q7}$) —P(O)(O$R^{r7}$)$_2$ or =$Q^{d5}$;

each $A^{a6}$, $A^{b6}$, $A^{c6}$, $A^{d6}$, $A^{e5}$, and $A^{f6}$ independently represents a single bond, —C(O)N($R^{s7}$)—, —N($R^{t7}$) or —O—;

each $Q^{a5}$, $Q^{b5}$, $Q^{c5}$, and $Q^{d5}$ independently represents =O, =S, =C(H)NO$_2$, =N(CN), =N$R^{u7}$, =NN($R^{v7}$)$R^{w7}$ or =N(O$R^{x7}$), or =NS(O)$_p$N($R^{v7}$)$R^{w7}$;

each $R^{a7}$ and $R^{f7}$ independently represents $C_{1-6}$ alkyl, $C_{2-6}$ alkenyl or $C_{2-6}$ alkynyl, each optionally substituted by one or more groups independently selected from $G^{6a}$, heterocyclyl optionally substituted by one or more groups independently selected from $G^{6b}$, aryl optionally substituted by one or more groups independently selected from $G^{6c}$, and heteroaryl optionally substituted by one or more groups independently selected from $G^{6d}$;

each $R^{b7}$, $R^{c7}$, $R^{d7}$, $R^{e7}$, $R^{g7}$, $R^{h7}$, $R^{i7}$, $R^{j7}$, $R^{k7}$, $R^{l7}$, $R^{m7}$, $R^{n7}$, $R^{o7}$, $R^{p7}$, $R^{q7}$, $R^{r7}$, $R^{s7}$, $R^{t7}$, $R^{u7}$, $R^{v7}$, $R^{w7}$ and and $R^{x7}$ independently represents H or $C_{1-6}$ alkyl, $C_{2-6}$ alkenyl or $C_{2-6}$, alkynyl, each optionally substituted by one or more groups independently selected from $G^{6a}$, heterocyclyl optionally substituted by one or more groups independently selected from $G^{6b}$, aryl optionally substituted by one or more groups independently selected from $G^{6C}$, and heteroaryl optionally substituted by one or more groups independently selected from $G^{6d}$, or alternatively any of $R^{c7}$ and $R^{d7}$, $R^{g7}$ and , $R^{h7}$, $R^{j7}$ and $R^{k7}$, $R^{n7}$ and $R^{o7}$ and/or $R^{v7}$, $R^{w7}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $G^{5a}$, $G^{5b}$, $G^{5c}$ and $G^{5d}$ independently represents halo, $R^{a8}$, —CN, -$A^{a7}$-C($Q^{a6}$)$R^{b8}$, -$A^{b7}$-C($Q^{b6}$)N($R^{c8}$)$R^{d8}$, -$A^{c7}$-C($Q^{c6}$)O$R^{e8}$, -$A^{d7}$-S(O)$_p$$R^{f8}$, -$A^{e7}$-S(O)$_p$N($R^{g8}$)$R^{h8}$, -$A^{f7}$-S(O)$_p$O$R^{i8}$, —N$_3$, —N($R^{j8}$)$R^{k8}$, —N(H)CN, —NO$_2$, —ONO$_2$, —O$R^{l8}$, —S$R^{m8}$—B(O$R^{n8}$)$_2$, —P(O)(N($R^{o8}$)$R^{p8}$)$_2$, —P(O)(N($R^{o8}$)$R^{p8}$)(O$R^{q8}$) —P(O)(O$R^{r8}$)$_2$ or =$Q^{d6}$;

each $A^{a7}$, $A^{b7}$, $A^{c7}$, $A^{d7}$, $A^{e7}$, and to $A^{f7}$ independently represents a single bond, —C(O)N($R^{s8}$)—, —N($R^{t8}$)— or —O—;

each $Q^{a6}$, $Q^{b6}$, $Q^{c6}$, and $Q^{d6}$ independently represents =O, =S, =C(H)NO$_2$, =N(CN), =N$R^{u8}$, =NN($R^{v8}$)$R^{w8}$, =N(O$R^{x8}$), or =NS(O)$_p$N($R^{v8}$)$R^{w8}$;

each $G^{6a}$, $G^{6b}$, $G^{6c}$ and $G^{6d}$ independently represents halo, $R^{a9}$, —CN, -$A^{a8}$-C($Q^{a7}$)$R^{b9}$, -$A^{b8}$-C($Q^{b7}$)N($R^{c9}$)$R^{d9}$, -$A^{c8}$-C($Q^{c7}$)O$R^{e9}$, -$A^{d8}$-S(O)$_p$$R^{f9}$, -$A^{e8}$-S(O)$_p$N($R^{g9}$) $R^{h9}$, -$A^{f8}$-S(O)$_p$O$R^{i9}$, —N$_3$, —N($R^{j9}$)$R^{k9}$, —N(H)CN, —NO$_2$, —ONO$_2$, —O$R^{l9}$, —S$R^{m9}$—B(O$R^{n9}$)$_2$, —P(O)(N($R^{o9}$)$R^{p9}$)$_2$, —P(O)(N($R^{o9}$)$R^{p9}$)(O$R^{q9}$) or —P(O)(O$R^{r9}$)$_2$ or =$Q^{d7}$;

each $A^{a8}$, $A^{b8}$, $A^{c8}$, $A^{d8}$, $A^{e8}$, and $A^{f8}$ independently represents a single bond, —C(O)N($R^{s9}$)—, —N($R^{t9}$)— or —O—;

each $Q^{a7}$, $Q^{b7}$, $Q^{c7}$, and $Q^{d7}$ independently represents =O, =S, =C(H)NO$_2$, =N(CN), =N$R^{u9}$, =NN($R^{v9}$)$R^{w9}$, =N(O$R^{x9}$), or =NS(O)$_p$N($R^{v9}$)$R^{w9}$;

each $R^{a8}$ and $R^{f8}$ independently represents H or $C_{1-6}$ alkyl optionally substituted by one or more F;

each $R^{b8}$, $R^{c8}$, $R^{d8}$, $R^{e8}$, $R^{g8}$, $R^{h8}$, $R^{i8}$, $R^{j8}$, $R^{k8}$, $R^{l8}$, $R^{m8}$, $R^{n8}$, $R^{o8}$, $R^{p8}$, $R^{q8}$, $R^{r8}$, $R^{s8}$, $R^{t8}$, $R^{u8}$, $R^{v8}$, $R^{w8}$ and $R^{x8}$ independently represents H or $C_{1-6}$ alkyl optionally substituted by one or more F, or alternatively any of $R^{c8}$ and $R^{d8}$, $R^{g8}$ and $R^{h8}$, $R^{j8}$ and $R^{k8}$, $R^{n8}$ and $R^{o8}$ and/or $R^{v8}$ and $R^{w8}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each $R^{a9}$ and $R^{f9}$ independently represents H or $C_{1-6}$ alkyl optionally substituted by one or more F;

each $R^{b9}$, $R^{c9}$, $R^{d9}$, $R^{e9}$, $R^{g9}$, $R^{h9}$, $R^{i9}$, $R^{j9}$, $R^{k9}$, $R^{l9}$, $R^{m9}$, $R^{n9}$, $R^{o9}$, $R^{p9}$, $R^{q9}$, $R^{r9}$, $R^{s9}$, $R^{t9}$, $R^{u9}$, $R^{v9}$, $R^{w9}$ and $R^{x9}$ independently represents H or $C_{1-6}$ alkyl optionally substituted by one or more F, or alternatively any of $R^{c9}$ and $R^{dg}$, $R^{g9}$ and $R^{h9}$, $R^{j9}$ and $R^{k9}$, $R^{n9}$ and $R^{o9}$ and/or $R^{v9}$ and $R^{w9}$, are linked together to form, together with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O; and each p independently represents 1 or 2, wherein a cancer is characterised by increased MYC activity when:
  (1) there is an at least 50% increase in the copy number of a MYC gene in a cancer cell from the patient compared to a corresponding non-cancerous cell from the patient; or
  (2) there is an at least 50% increase in MYC mRNA or protein levels in a cancer cell from the patient compared to a corresponding non-cancerous cell from the patient; or
  (3) there is an at least 50% increase in activity of a MYC pathway in a cancer cell from the patient compared to a corresponding non-cancerous cell from the patient, and wherein the cancer characterised by increased MYC activity is selected from Burkitt's lymphoma, ovarian cancer, basel-like breast cancer, esophageal squamous cell carcinoma, colon cancer, endometrial cancer, neuroblastoma, small cell lung carcinoma, medulloblastoma, pancreatic cancer, head and neck cancer, prostate cancer, and hepatocellular carcinomas.

2. The method of claim 1, wherein $R^1$ represents:
phenyl optionally substituted by one or more groups independently selected from $G^{1c}$;
or pyridinyl optionally substituted by one or more groups independently selected from $G^{1d}$.

3. The method of claim 1, wherein each $G^{1c}$ and $G^{1d}$ dependently represents halo, $R^{a4}$, —N($R^{j4}$)$R^{k4}$ or —O$R^{14}$.

4. The method of claim 1, each $G^{1c}$ and $G^{1d}$ dependently represents:
  $C_{1-8}$ alkyl optionally substituted by one or more groups independently selected from $G^{4a}$; —N($R^{j4}$)$R^{k4}$; or —O$R^{14}$.

5. The method of claim 1, wherein the compound of formula I is a compound of formula Ia

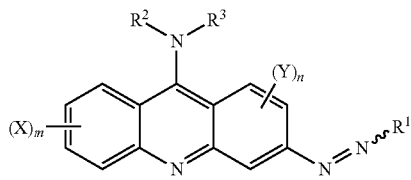

Ia or a compound of formula Ia'

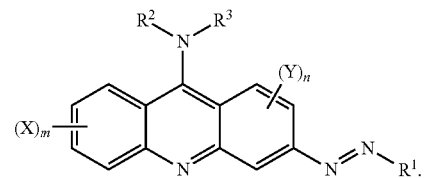

Ia'

6. The method of claim 1, wherein n represents 0.

7. The method of claim 1, wherein m represents 1, 2, or 3.

8. The method of claim 1, wherein m represents 1.

9. The method of claim 1, wherein the compound of formula I is a compound of formula Ib

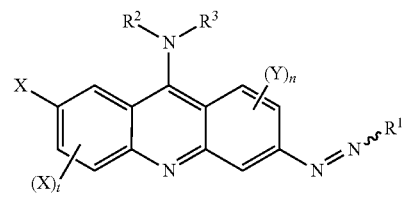

Ib or a compound of formula Ib'

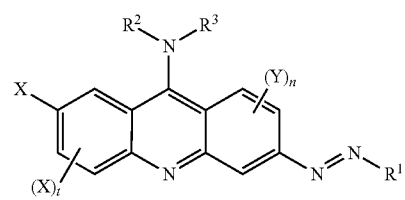

Ib' wherein t represents 0, 1, 2 or 3.

10. The method of claim 1, wherein each $R^{12}$ represents $C_{1-6}$ alkyl optionally substituted by one or more groups independently selected from $G^{3a}$.

11. The method of claim 1, wherein each $R^{12}$ represents $C_2$ alkyl optionally substituted by one or more fluoro.

12. The method of claim 1, wherein the cancer is characterised by increased MYC activity when there is an at least 50% increase in MYC mRNA or protein levels in a cancer cell from the patient compared to a corresponding non-cancerous cell from the patient.

* * * * *